(12) United States Patent
Redden et al.

(10) Patent No.: US 9,658,201 B2
(45) Date of Patent: May 23, 2017

(54) METHOD FOR AUTOMATIC PHENOTYPE MEASUREMENT AND SELECTION

(71) Applicant: Blue River Technology Inc., Mountain View, CA (US)

(72) Inventors: Lee Kamp Redden, Stanford, CA (US); Matthew Colgan, Mountain View, CA (US)

(73) Assignee: Blue River Technology Inc., Mountain View, CA (US)

( * ) Notice: Subject to any disclaimer, the term of this patent is extended or adjusted under 35 U.S.C. 154(b) by 431 days.

(21) Appl. No.: 14/329,161

(22) Filed: Jul. 11, 2014

(65) Prior Publication Data

US 2015/0015697 A1     Jan. 15, 2015

Related U.S. Application Data

(60) Provisional application No. 61/844,967, filed on Jul. 11, 2013, provisional application No. 61/859,091, (Continued)

(51) Int. Cl.
    *G01N 33/00*         (2006.01)
    *G06K 9/62*          (2006.01)

(52) U.S. Cl.
    CPC ....... *G01N 33/0098* (2013.01); *G06K 9/6202* (2013.01); *G06K 2209/17* (2013.01)

(58) Field of Classification Search
    None
    See application file for complete search history.

(56) References Cited

U.S. PATENT DOCUMENTS 3,892,357 A    7/1975   Tamny
4,015,366 A    4/1977   Hall, Iii
(Continued)

FOREIGN PATENT DOCUMENTS

CN      102166548 B    10/2012
DE      19523648 A1    1/1997
(Continued)

OTHER PUBLICATIONS

Sirault et al. WO2013082648A1.*
(Continued)

*Primary Examiner* — Matthew Bella
*Assistant Examiner* — Soo Shin
(74) *Attorney, Agent, or Firm* — Fenwick & West LLP

(57) ABSTRACT

A system for plant parameter detection, including: a plant morphology sensor having a first field of view and configured to record a morphology measurement of a plant portion and an ambient environment adjacent the plant, a plant physiology sensor having a second field of view and configured to record a plant physiology parameter measurement of a plant portion and an ambient environment adjacent the plant, wherein the second field of view overlaps with the first field of view; a support statically coupling the plant morphology sensor to the physiology sensor, and a computing system configured to: identify a plant set of pixels within the physiology measurement based on the morphology measurement; determine physiology values for each pixel of the plant set of pixels; and extract a growth parameter based on the physiology values.

30 Claims, 11 Drawing Sheets

Related U.S. Application Data filed on Jul. 26, 2013, provisional application No. 61/942,740, filed on Feb. 21, 2014, provisional application No. 62/004,722, filed on May 29, 2014.

(56) References Cited

U.S. PATENT DOCUMENTS

| | | | |
|---|---|---|---|
| 4,755,942 A † | 7/1988 | Gardner | |
| 5,222,324 A | 6/1993 | O'Neall et al. | |
| 5,296,702 A | 3/1994 | Beck et al. | |
| 5,442,552 A | 8/1995 | Slaughter et al. | |
| 5,453,618 A | 9/1995 | Sutton et al. | |
| 5,507,115 A | 4/1996 | Nelson | |
| 5,585,626 A | 12/1996 | Beck et al. | |
| 5,606,821 A | 3/1997 | Sadjadi et al. | |
| 5,621,460 A | 4/1997 | Hatlestad et al. | |
| 5,661,817 A | 8/1997 | Hatlestad et al. | |
| 5,768,823 A | 6/1998 | Nelson | |
| 5,789,741 A | 8/1998 | Kinter et al. | |
| 5,793,035 A | 8/1998 | Beck et al. | |
| 5,809,440 A | 9/1998 | Beck et al. | |
| 5,837,997 A | 11/1998 | Beck et al. | |
| 5,884,224 A | 3/1999 | McNabb et al. | |
| 5,911,668 A | 6/1999 | Auerbach et al. | |
| 5,924,239 A | 7/1999 | Rees et al. | |
| 6,160,902 A † | 12/2000 | Dickson | |
| 6,199,000 B1 | 3/2001 | Keller et al. | |
| 6,212,824 B1 * | 4/2001 | Orr | A01G 7/00 209/576 |
| 6,336,051 B1 | 1/2002 | Pangels et al. | |
| 6,553,299 B1 | 4/2003 | Keller et al. | |
| 6,574,363 B1 | 6/2003 | Classen et al. | |
| 6,671,582 B1 | 12/2003 | Hanley | |
| 6,837,617 B1 * | 1/2005 | Koltunov | G01J 5/60 250/208.1 |
| 6,919,959 B2 | 7/2005 | Masten | |
| 6,999,877 B1 | 2/2006 | Dyer et al. | |
| 7,032,369 B1 | 4/2006 | Eaton et al. | |
| 7,212,670 B1 | 5/2007 | Rousselle et al. | |
| 7,248,968 B2 | 7/2007 | Reid | |
| 7,313,268 B2 | 12/2007 | Luo et al. | |
| 7,408,145 B2 | 8/2008 | Holland | |
| 7,412,330 B2 | 8/2008 | Spicer et al. | |
| 7,570,783 B2 | 8/2009 | Wei et al. | |
| 7,580,549 B2 | 8/2009 | Wei et al. | |
| 7,684,916 B2 | 3/2010 | Wei et al. | |
| 7,715,013 B2 | 5/2010 | Glaser et al. | |
| 7,716,905 B2 | 5/2010 | Wilcox et al. | |
| 7,721,515 B2 | 5/2010 | Pollklas et al. | |
| 7,723,660 B2 | 5/2010 | Holland | |
| 7,792,622 B2 | 9/2010 | Wei et al. | |
| 7,876,927 B2 | 1/2011 | Han et al. | |
| 7,877,969 B2 | 2/2011 | Behnke | |
| 7,894,663 B2 | 2/2011 | Berg et al. | |
| 7,904,218 B2 | 3/2011 | Jochem et al. | |
| 7,911,517 B1 | 3/2011 | Hunt, Jr. et al. | |
| 8,027,770 B2 | 9/2011 | Poulsen | |
| 8,028,470 B2 | 10/2011 | Anderson | |
| 8,265,835 B2 | 9/2012 | Peterson et al. | |
| 8,537,360 B2 | 9/2013 | Stachon et al. | |
| 2003/0009282 A1 | 1/2003 | Upadhyaya et al. | |
| 2003/0019949 A1 | 1/2003 | Solie et al. | |
| 2007/0044445 A1 * | 3/2007 | Spicer | G01B 11/24 56/10.1 |
| 2008/0141585 A1 | 6/2008 | Benfey et al. | |
| 2009/0210119 A1 | 8/2009 | Poulsen | |
| 2010/0215222 A1 | 8/2010 | Zeelen et al. | |
| 2010/0322477 A1 | 12/2010 | Schmitt et al. | |
| 2011/0041399 A1 | 2/2011 | Stachon et al. | |
| 2011/0135161 A1 * | 6/2011 | Koutsky | A01H 1/04 382/110 |
| 2011/0167721 A1 | 7/2011 | Lejeune et al. | |
| 2011/0211733 A1 | 9/2011 | Schwarz | |
| 2012/0101784 A1 | 4/2012 | Lindores et al. | |
| 2012/0169504 A1 | 7/2012 | Hillger et al. | |
| 2012/0237083 A1 | 9/2012 | Lange et al. | |
| 2013/0291138 A1 | 10/2013 | Feng et al. | |
| 2014/0107957 A1 | 4/2014 | Lindores et al. | |
| 2014/0180549 A1 | 6/2014 | Siemens et al. | |
| 2015/0134152 A1 * | 5/2015 | Coram | G01N 33/0098 701/3 |

FOREIGN PATENT DOCUMENTS

| | | |
|---|---|---|
| WO | 9717830 A1 | 5/1997 |
| WO | 0003589 A1 | 1/2000 |
| WO | 2011119403 A | 9/2011 |
| WO | 2012094116 A1 | 7/2012 |

OTHER PUBLICATIONS

PCT International Search Report and Written Opinion for PCT/US2014/046320, Jan. 9, 2015, 10 Pages.

Bellasio, C., et al., "Computer Reconstruction of Plant Growth and Chlorophyll Fluorescence Emission in Three Spatial Dimensions", Sensors, vol. 12, No. 12, Jan. 18, 2012, pp. 1052-1071.

Busemeyer, L., et al., "Breed Vision—A Multi-Sensor Platform for Non-Destructive Field-Based Phenotyping in Plant Breeding," Sensors, Feb. 27, 2013, vol. 13, No. 3, pp. 2830-2847.

Dhondt, S., et al., "Cell to whole-plant phenotyping: the best is yet to come," Trends in Plant Science, May 23, 2013, vol. 18, No. 8, pp. 428-439.

Omasa, K., et al., "3D lidar imaging for detecting and understanding plant responses and canopy structure", Journal of Experimental Botany, Nov. 30, 2006, vol. 58, No. 4, pp. 881-898.

Yoon, S.C., et al., "Stereo Spectral Imaging System for Plant Health Characterization," An ASABE Meeting Presentation, Written for presentation at the 2009 ASABE Annual International Meeting Sponsored by ASABE Grand Sierra Resort and Casino, Jun. 21-Jun. 24, 2009, pp. 1-12.

European Search Report for European Patent Application No. EP 14822583, Apr. 10, 2017, 9 pages.

Rascher, Uwe et al., "Non-invasive approaches for phenotyping of enhanced performance traits in bean," Functional Plant Biology, 38: 968-983, published Dec. 1, 2011, www.publish.csiro.au/journals/fbp.†

Chaerle, Laury et al., "Multi-sensor plant imaging: Towards the development of a stress catalogue," Biotechnology Journal, 4: 1152-1167, Mar. 31, 2009, Wiley-VCH Verlag GmbH & Co. KGaA, Weinheim, Germany.†

\* cited by examiner
† cited by third party

METHOD FOR AUTOMATIC PHENOTYPE MEASUREMENT AND SELECTION

CROSS-REFERENCE TO RELATED APPLICATIONS

This application claims priority to U.S. Provisional Application Nos. 61/844,967 filed 11 Jul. 2013, 61/859,091 filed 26 Jul. 2013, 61/942,740 filed 21 Feb. 2014, and 62/004,722 filed 29 May 2014, which are incorporated in their entireties by this reference.

This application is related to U.S. application Ser. No. 13/788,320 filed 7 Mar. 2013, which is incorporated in its entirety by this reference.

TECHNICAL FIELD

This invention relates generally to the agricultural field, and more specifically to a new and useful automated system and method of plant measurement and selection in the agricultural field.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System.

Figure 1:
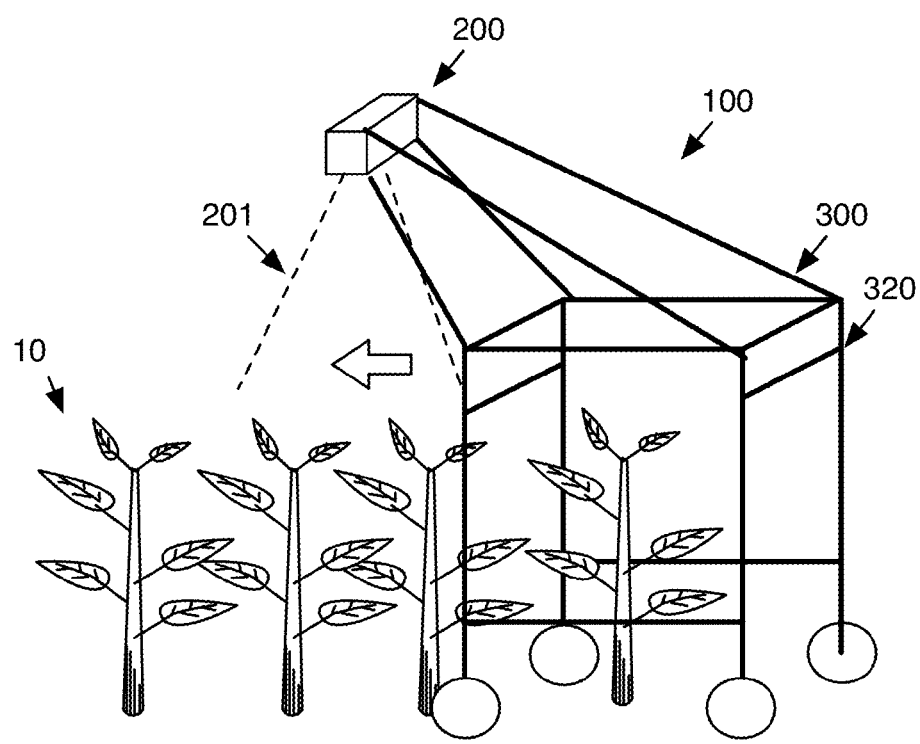
FIG. 1 is a schematic representation of a variation of the system in operation.

As shown in FIG. 1, the system 100 preferably includes a detection mechanism 200 configured to detect a plant within a plant field and a computing system. More preferably, the system includes a plant morphology sensor, a plant physiology sensor, a support statically coupling the plant geometry sensor to the plant physiology sensor, and a computing system. The system can additionally include an ambient environment sensor or any other suitable component. The system is preferably an improvement to the system described in U.S. application Ser. No. 13/788,320 filed 7 Mar. 2013 (hereinafter U.S. application '320), which is incorporated in its entirety by this reference. However, the system can be similar to that of U.S. application '320 without the nozzles, be a hand carried system, an aerial system, or any other suitable system.

The system functions to measure plant data. More preferably, the system measures plant morphology (plant geometry). The system can additionally function to measure plant physiology, wherein the plant physiology values are preferably corrected by (e.g., normalized by) the geometry measurements to obtain physiological parameter values for the plant 10. Plant indices are preferably extracted from the plant morphological and/or physiological parameters, but can alternatively or additionally be extracted from other plant data. The system functions to measure the parameters on a plant-by-plant basis, but can alternatively measure the parameters for a set of plants. The system can additionally function to generate recommendations (e.g., treatment recommendations on a geographic area or plant level, etc.), notifications (e.g., for growth or other events), or any other suitable information.

The system can additionally function to traverse through a geographic area, such as a field. The system is preferably a ground-based system, but can alternatively be an airborne system or any other suitable system. The system 10 can be configured (e.g., be sized) to span at least a first and a second crop furrow (e.g., encompass a crop row); be configured to translate along a single furrow; be configured to translate between stems of adjacent plants (e.g., sized on the order of several inches); be configured to encompass an entire or substantial portion of a crop field, or have any other suitable dimension. The system is preferably a passive system, and removably or permanently mounts to a driving mechanism, such as a tractor, that applies a driving force (e.g., a pulling or pushing force) to translate the system within the geographic area. Alternatively, the system can be an active system, and translate within the geographic area automatically or in response to receipt to driving instructions. In a specific variation, the system is driven toward a direction opposing the direction of sun irradiance, toward the sun, at an angle relative to the direction of sun irradiance (e.g., within 45 degrees of the sun irradiance vector), or at any other suitable angle. For example, if the sun is in the east, the system is preferably driven eastward. However, the system can be otherwise controlled.

In operation, the system preferably moves through a geographic area (e.g., a plant field) and performs the method. The system preferably traverses through the field at a substantially constant velocity, but can alternatively traverse through the field at a substantially constant acceleration, at an irregular velocity, irregular acceleration, constant plant or feature count, or at any other suitable speed. In one variation, the system is automatically driven through the geographic area. In another variation, the system is driven through the geographic area by a drive mechanism such as a tractor, wherein the drive mechanism is preferably separate but can alternatively be integrated into the system. In this variation, the system can additionally include a coupling mechanism, such as a hitch, that couples the system to the drive mechanism.

This system and method confer several benefits over conventional systems. First, the system and method enable non-destructive plant data collection in-situ (e.g., in a natural plant field exposed to natural sunlight), wherein the plant remains rooted to the ground during plant data collection. By leveraging a combination of morphological and physiological measurements, this system and method further alleviate the problems associated with collecting plant data in-situ. For example, the ambient environment can introduce noise into physiological measurements. In a specific example, when a multispectral image is captured for a given plant, the substrate 20 (soil) surrounding the plant 10 also reflects the wavelengths of interest. This results in two issues: first, the plant index value extracted from the multispectral image will be for the entire image, which includes both the plant 10 and the surrounding substrate 20; second, the plant index value for each pixel associated with a plant includes both the plant index value resulting from the plant and the index value resulting from the substrate (e.g., wherein the light of interest penetrates through the plant 10 and reflects off the substrate, back through the plant 10, to the sensor). By determining the boundaries and/or pixels associated with the plant 10, the system can determine the plant index value for only the plant, and normalize the determined plant index value by the interference from the substrate 20. Furthermore, the system and method offers flexibility in the plant growth environment, wherein the system and method can be used in a controlled environment, such as a greenhouse, or in any other suitable environment.

Second, the system and method enable real-time data collection and analysis while traversing through a geographic location. Collecting and analyzing data from multiple sensors while moving introduces measurement correlation problems, arising from timing issues, odometry issues, and sensor shift issues. This system and method resolves this issue by leveraging plant identifiers, such as geographic locations, to correlate measurements from different sensors. In one variation, the system and method further address the sensor shift issue by arranging one sensor within the field of view of a second sensor, such that sensor shift between sequential measurements can be identified and corrected for during measurement analysis.

Third, this system and method addresses signal interference problems experienced by conventional systems. The system and method addresses this issue by using narrowband physiological parameter measurements (e.g., narrowband multispectral sensors), such that the overlap between monitored wavelength bands are minimized.

Fourth, passive variations of the system that are configured to operate based on ambient light and are operable without an auxiliary light source confer light source benefits and geographic range benefits. For example, the system can utilize incident sunlight as the light source, and does not include an auxiliary artificial light source to provide the light for the physiological sensors. By leveraging ambient light (e.g., measuring ambient light reflected by the plant 10), this system reduces issues stemming from ambient light interference with artificial light. Leveraging ambient light also has the added benefit of having increased light intensity, as the sun can be brighter than conventional artificial light sources. By leveraging ambient light and reducing the number of artificial light sources, this system alleviates power provision issues, as artificial light sources require increased power storage mechanisms for power provision. Reducing the amount of power storage required for the system can have the added benefit of reducing system weight, thereby reducing fuel consumption during system mobilization. Reducing the amount of power storage required for the system can also have the added benefit of increasing the range of the system, since the range is no longer limited by the amount of power that can be stored on-board the system. This system can additionally include a light sensor that measures the amount of incident light, and adjusts the resultant plant index values based on the amount of incident light. This can function to confer the benefit of being operable even under cloudy conditions, which conventional systems are incapable of.

Fifth, by identifying the pixels of interest (plant pixels), the system and method can reduce the number of physiology pixels that must be processed, thereby reducing the processing time and resources required to process large numbers of physiology measurements.

The system and method function to collect plant data for plant index value determination, and can additionally output plant index values, which function to describe the health of a plant 10. The plant index values can be determined for a portion of the plant 10 (e.g., plant boundaries, leaves, stem, roots, flowers, fruits, apical meristem, apex, nodes, buds, etc.), for the plant as a whole, for a portion of the plant field, for the entirety of the plant field (e.g., geographic area), or for any other suitable plant portion, plant, or set of plants. Plant index values can be determined for a single time point or can be tracked using multiple measurements over an extended period of time (e.g., at different periods during the growth cycle), wherein individual plants can be uniquely identified with a plant identifier.

The plant index values are preferably data indicative of desired plant characteristics, such as pest resistance, disease resistance, hardiness, yield, competition, or any other suitable characteristic. The plant characteristics are preferably determined by a breeder, but can alternatively be determined by a farmer, automatically by the system (e.g., in response to receipt of a desired outcome from a user), or determined in any other suitable manner.

Plant indices (vegetative indices) can include Normalized Difference Vegetation Index (NDVI), Transformed Chlorophyll Absorption in Reflectance Index normalized by Optimized Soil-Adjusted Vegetation Index (TCARI/OSAVI), Normalized Difference Red Edge Index (NDRE), Canopy Chlorophyll Content Index (CCCI), Photochemical Reflectance Index (PRI), crop water stress index (CWSI), canopy temperature less air temperature (Tc−Ta), stomatal conductance (G), stem water potential, water stress, water content, Water Band Index (WBI), plant uniformity across the geographic area, Leaf Area Index (LAI), Net Assimilation Rate (NAR), Relative Growth Rate (RGR), Leaf Area Ratio (LAR), Leaf Area Duration (LAD), Crop Growth Rate (CGR), plant index value change over time, plant index value change rate, absolute growth rate in volume, absolute growth rate in number, absolute growth rate in mass, or any other suitable plant index.

The plant index values are preferably determined from plant data collected from the plant 10. The plant data preferably includes plant morphological data (structural data, geometric data) and plant physiological data (plant functionality data), but can alternatively or additionally include plant ecological data (e.g., data indicative of interactions with the ambient environment), phytochemistry (biochemistry of the plants), cell biology, genetics, biophysics, molecular biology, or any other suitable plant data. The plant index can be determined (e.g., calculated, selected from a chart, or graph, etc.) based on the plant morphology measurement, the plant physiology measurement, only the plant morphology measurement, only the plant physiology measurement, a combination of a set of plant morphology measurements (e.g., one or more plant morphology measurements) and a set of plant physiology measurements (e.g., one or more plant physiology measurements), only a combination of one plant morphology measurement and one plant physiology measurement, a combination of the plant morphology measurement and a set of ambient environment measurements, a combination of the plant physiology measurement and a set of ambient environment measurements, a combination of a set of plant morphology measurements, a set of plant physiology measurements, and a set of ambient environment measurements (e.g., location, temperature, humidity, light, etc.), or determined based on any other suitable variable.

The collected plant data is preferably optical data, but can alternatively be reflectance data, x-ray data, thermal emission, audio data (e.g., ultrasonic data, etc.), haptic data, chemical data (e.g., chemical composition of the plant), electric data (e.g., resistivity, voltage open circuit, inductance, electrical noise, conductance, etc.), responsiveness or response to an applied stimulus (e.g., incident light, acoustic noise, haptic stimulus, electric stimulus), thermal data, or any other suitable plant data. The collected signals can be within the range of human detection, but can alternatively or additionally be determined based on signals outside the range of human detection. For example, measurements can be taken using or recording an audio frequency outside the aural frequency range or a light frequency outside the visual spectrum. The plant data can additionally or alternatively be chemical characteristics (e.g., chemical composition, concentration of a given chemical, etc.), visual characteristics, electrical characteristics, or any other suitable characteristic of the plant 10.

Examples of characteristics that can be extracted include the plant size, the plant color, the color distribution over the plant, the estimated plant height, plant volume, plant mass, the plant density (e.g., mass/volume), whether the plant reflects (or absorbs) a lightwave of a specific frequency, the sugar concentration of the plant 10, the sugar distribution over the entirety of the plant 10, the plant crown diameter, the leaf size, the projected leaf area, the inferred leaf area, the stand count, the uniformity of the leaves (e.g., in size, shape, color, density), leaf area, leaf temperature, plant conductivity, leaf mass index, leaf color, leaf color distribution, leaf texture, leaf edge roughness, leaf fuzziness, tassel length, stem woodiness, stem chemical composition, stem, stock, or trunk width, stem elasticity, fruit size, fruit color, fruit sugar concentration, fruit water content, number of fruits per plant, fruit distribution over the plant, fruit skin thickness, fruit weight, fruit density, fruit turgidity, fruit smell (e.g., concentration of predetermined aromatic compounds emitted by the fruit), number of grains, grain moisture, grain compound content (e.g., protein, oil, mineral, vitamin, etc.), the position of a plant component (e.g., leaves, stems, fruit, etc.) relative to the plant or an adjacent plant, root distribution, root aeration, root depth, root thickness, or any other suitable plant characteristic.

The plant data is preferably collected from the entirety of the plant field, but can alternatively be collected from a portion (e.g., less than the entirety) of the plant field. The plant data is preferably non-destructively collected from the plants, but can alternatively be destructively collected from a plant. The plant data is preferably collected over multiple sessions, spaced over a period of time, such that the plant characteristics are tracked across time. However, the plant data can be collected at any other suitable frequency. The plant data for a plant is preferably measured at predetermined intervals over the ontogeny of the plant, but can alternatively be measured at any other suitable frequency. More preferably, the plant data for all the plants within a plant field portion are collected in a single session, and multiple sessions are performed for each plant field portion. The multiple sessions are preferably performed at predetermined intervals, wherein the growth stage of each plant 10 is preferably later determined from the collected plant data. Alternatively, the average growth stage for the plants within the plant field portion can be estimated, wherein a session is initiated for the plant field portion in response to the average growth stage for the plant field portion reaching a predetermined growth stage. However, each session can alternatively be performed at each treatment stage or at any other suitable frequency.

The plant index values or plant data can additionally or alternatively be used to determine population-level data for the geographic area (e.g., plant field portion). Examples of population-level data include leaf-area index, evapotranspiration, estimated average flowering time across the plant population, or any other suitable variable or parameter. Furthermore, because large numbers of plants can be measured at such high resolution across the population, the relatively minor effect of quantitative trait loci (QTL) can be enhanced and detected. The large number of plants can additionally be used to form a baseline index value for comparison to the index value of a given plant 10. For example, chlorosis can be detected in a first plant if the respective levels of reflected green light are lower than the neighboring plants or the median green light reflectivity of the plant population.

The plant index values or plant data can additionally or alternatively be used to automatically select plants that express desired phenotypes from the plurality of plants within the plant field. The identified plants are preferably used for successive breeding, wherein the genetic material of the selected plants is preferably used in the creation of the next generation of plants (e.g., by sexual reproduction, genetic vector methods, etc.). Alternatively, the identified plants can be asexually reproduced, such as by taking a cutting and grafting the cutting onto a host plant or by using stem or tuber cuttings. The phenotypic data can additionally or alternatively be used to test individual plant reactions to given treatments or management systems, wherein specific plant phenotypes that are susceptible (or, conversely, resistant) to the given treatment can be identified and selected from a field of plants. Individual plant reactions to given treatments can additionally be used to inform future planting or cropping decisions. The phenotypic data can additionally or alternatively be used to determine individual plant growth patterns in a given environment (e.g., in the plant microclimate), wherein plant genotypes that express the desired phenotypes (or conversely, do not express the desired phenotype) can be identified and selected from a field of plants. The selected plants can be subsequently recommended to growers planting in environments having predicted environmental parameters similar to the plant microclimate. The selected plants can alternatively be subsequently recommended to growers planting with management systems similar to the plant management system and/or plan. The plant data (e.g., plant indices) can additionally or alternatively be used to determine treatment parameters for one or more plants, such as which plants to treat, when to treat the plants, which treatment method to use, where on each plant to treat, how much of a treatment to use (e.g., what concentration of fertilizer should be used), or any other suitable treatment parameter. The treatments can include growth promotion, growth retardation, necrosis, or any other suitable treatment.

The system and method can additionally function to measure and/or process environmental data. Environmental data can include soil data, ambient air data, ambient light data, location data, or any other suitable data. Examples of environmental data that can be collected includes soil pH, soil particle size, soil compaction, soil drainage, soil color, soil temperature, soil moisture, soil texture, soil organic matter content, soil nutrient and chemical composition data (e.g., nitrogen concentrations), air humidity data, ambient light data (e.g., incident radiation, photoperiod, etc.), ambient barometric pressure, ambient cloud coverage, ambient wind speed, gas emissions (e.g., adjacent air chemical composition), surrounding plant data (e.g., other plants that are grown in the same plant field or adjacent the plant of interest), or any other suitable data for the environment surrounding each plant 10. The environmental data can be extracted from the plant data, be determined using the plant detection mechanism(s) 200, or can be determined from auxiliary sensor data, wherein the system preferably additionally includes auxiliary sensors.

Environmental characteristics or parameters can be determined (e.g., extracted, processed, calculated, etc.) based on the environmental data. The extracted environmental characteristics are preferably indicative of environmental factors that influence plant growth and/or are influenced by plant growth, but can alternatively be indicative of any other suitable factor. The environmental characteristics are preferably determined from the measured environmental data, but can alternatively be determined from the measured plant data, be the environmental data, or be determined in any other suitable manner. Environmental characteristics that can be extracted include estimated plant moisture levels (e.g., based on the difference between ambient temperature and the plant temperature), soil moisture levels (e.g., from the reflectivity or darkness of the soil surrounding the plant 10), light levels (e.g., based on the actual vs. expected contrast in the image), type of soil (e.g., based on analysis of the background granularity, color distribution, etc.), soil chemistry (e.g., based on the soil color, chemical monitor data, surrounding insect and plant parameters, etc.), the amount of growing space (e.g., clear space) around the plant, distance to the closest plant neighbors, the number and/or type of insects on the plant or in the soil, the number and/or size of neighboring plants, the chemical composition of the ambient environment surrounding the plant (e.g., gasses emitted by the plant), disease indicators, or any other suitable environmental characteristic.

The system and/or method can additionally function to leverage historical data. Historical data can include historical weather data (e.g., for the geographic area of the plant field or the plant), historical treatment data, historical planting data, or any other suitable historical data. The treatments can be applied and recorded as population treatments (e.g., the plant field was indiscriminately blanketed with the treatment), area treatments (e.g., rows 1-8 had a first treatment while rows 9-16 had a second treatment), or individual treatments (e.g., individual plants within the same row or plant field can be treated with different treatments, wherein the individual treatments can be manually or automatically applied by the system). Treatments can include fertilization, necrosis inducement, fungicide application, pesticide application, fruit harvesting, drought, chemical application, water application, plant hormone application, salinity control, disease exposure, insect infestation exposure, distance from plant to plant and population, genetics, epigenetics, planting depth, planting depth control, a combination of the aforementioned treatments, or any other suitable plant treatment.

The plants are preferably crops, but can alternatively be weeds or any other suitable plant 10. The crop is preferably corn, but can alternatively be lettuce, soy beans, rice, carrots, tomatoes, broccoli, cabbage, potatoes, wheat or any other suitable commercial crop. The plant field in which the method is used is preferably an outdoor plant field, but can alternatively be plants within a greenhouse, a laboratory, a grow house, a set of containers, a machine, or any other suitable environment. The plants are preferably grown in one or more plant rows (e.g., plant beds), wherein the plant rows are preferably substantially parallel, but can alternatively be grown in a set of plant pots, wherein the plant pots can be ordered into rows or matrices or be randomly distributed, or be grown in any other suitable configuration. The crop rows are preferably spaced between 2 inches to 45 inches apart (e.g., as determined from the longitudinal row axis), but can alternatively be spaced any suitable distance apart. The plants within each plant field, plant row, or plant field subdivision preferably includes the same type of crop (e.g., same genus, same species, etc.), but can alternatively include multiple crops (e.g., a first and a second crop), both of which are to be analyzed.

The plants 10 are preferably identified by plant identifiers. The plant identifiers are preferably unique, but can alternatively be non-unique and shared. The plant identifiers can be plant features, ambient environment features, or a secondary marker. The plant identifier can be a geographic location, a branch or leaf growth pattern from a stem, leaf edge irregularities or border patterns, leaf discoloration, stem cell arrangement, neighboring plant arrangement, a soil marker (e.g., a tag or probe), an RFID or other near-field communication tag, an artificially created plant feature (e.g., a brand), a time signal (e.g., time duration from a marker), or any other suitable plant identifier.

1. System.

The detection mechanism 200 of the system functions to measure signals indicative of plant data, such as measurements indicative of plant structure, physiology, and/or function. The system preferably includes one or more detection mechanisms. Multiple detection mechanisms are preferably arranged in series along a drive axis, such that the detection mechanisms sequentially encounter a given plant. Alternatively, multiple detection mechanisms can be arranged such that the set of detection mechanisms concurrently encounter and measure the parameters of the same plant. The arrangement of the detection mechanisms on the system is preferably tailored for different plant species (e.g., the system is in a first configuration for corn and a second configuration for lettuce), but can alternatively have the same configuration for every plant species.

The detection mechanism 200 preferably includes a sensor (receiver) that can capture signals for and/or generate a two-dimensional image (e.g., a top-down image), a three-dimensional image (e.g., of the entire plant, of the portion of the plant aboveground, of the portion of the plant below ground, etc.), or any other suitable image. Alternatively, the detection mechanism 200 can capture a spectral fingerprint (e.g., spectral image) or aural fingerprint of the plant. The detection mechanism 200 preferably generates frames of pixel data, but can alternatively generate waveforms or any other suitable signal. The detection mechanism measurements are preferably processed using structure from motion techniques into three-dimensional records (e.g., by tracking unique plant features, corners, non-unique features, etc. across sequential frames of the detection mechanism measurement), but can alternatively be processed using any other suitable technique.

The detection mechanism 200 preferably has a field of view (FOV) 201 or angle of view, wherein the detection mechanism records signals received from the field of view. The field of view 201 is preferably fixed relative to the field of view of a second sensor or another component of the system, but can alternatively have an adjustable field of view. The field of view 201 can be adjusted based on the distance of the sensor from the plant, or based on any other suitable imaging parameter. The field of view is preferably associated with a direction, wherein the field of view direction is preferably determined based on the position of the field of view relative to the sensor (e.g., the field of view direction is the sensor direction).

The detection mechanism 200 can additionally include a power source 500 that functions to power the detection mechanism, sensors, and/or emitters. The power source can be mounted in the same housing as the detection mechanism (e.g., wherein each detection mechanism 200 includes a power source), mounted remote from the detection mechanism, or located in any other suitable configuration. The system can include a single power source that powers multiple sensors and/or emitters, or can include multiple distributed power sources.

The detection mechanism 200 is preferably an imaging system, but can alternatively be an audio system, chemical monitoring system (e.g., a nitrogen sensor, pH sensor, etc.), radiation system (e.g., x-ray, gamma ray, or other radiation system), a thermocouple, a haptic system, an electric system, an electromagnetic system, a combination of the above, or any other suitable system.

The detection mechanism preferably measures signals reflected off subjects within the field of view of the detection mechanism, but can alternatively measure signals unobstructed by the subjects, generated by the subjects, or measure any other suitable signal. The subjects can include plants, substrate 20 (e.g., soil), or any other suitable subject within the detection mechanism's field of view. The signals can include light signals (e.g., wherein light properties can be measured, such as wavelength, amplitude, etc.), audio signals (e.g., herein audio properties can be measured, such as wavelength, amplitude, etc.), electric signals (e.g., generated by a force-feedback system, the plant, etc.), or any other suitable signal.

The detection mechanism is preferably passive, wherein the measured signals are generated by ambient sources. For example, the light measured by the detection mechanism can be ambient sunlight or another ambient light source. In another example, the chemical composition measured by the detection mechanism can be generated by the plant.

The detection mechanism can alternatively be an active system, wherein the detection mechanism can additionally or alternatively measure artificial signals (e.g., artificial light) that are provided by the system. In this variation, the detection mechanism can additionally include an emitter that provides the artificial signals. The artificial signals are preferably directed into the geographic area monitored by the detection mechanism field of view, but can alternatively be directed to any other suitable area. The emitter can be directed in the same direction as the detection mechanism, can be directed toward the detection mechanism, or be directed in any other suitable direction. The emitters are preferably configured to emit a signal within a given angular range of a gravity vector (e.g., at the top of a plant), but can alternatively be configured to emit a signal within a given angular range of a vector perpendicular to the gravity vector (e.g., at the side of a plant), configured to emit a signal parallel to the sensor field of view vector (e.g., vector perpendicular to a sensor plane), configured to be adjustable, or arranged in any suitable configuration. The signal can be substantially constant, modulated, pulsed, or otherwise controlled. The artificial emitter can be associated with the receiver, or can be associated with a second receiver, wherein both the first and second receivers measure signals emitted by a single source. For example, the receiver can include a narrow-band multispectral sensor that measures the light reflected by a plant of interest, wherein the light was emitted by a LIDAR system (e.g., emitting light at approximately 900 nm). The artificial emitter can be a light source, audio source, or any other suitable signal source. The artificial light source can be a narrow-band light (e.g., emit a narrow band of light wavelengths), a multi-spectral light (e.g., emit light along multiple light wavelengths), or any other suitable emitter. For example, the detection mechanism can include one or more light emitting elements (e.g., RGB LEDs, deep red LEDs, cyan LEDs, etc.) arranged in clusters, arrays, or any other suitable arrangement. The artificial audio source (audio emitter) can emit ultrasound, radar, or any other suitable audio signal. However, any other suitable artificial signal source can be used with a corresponding signal receiver.

In one variation of the system, the detection mechanism is an imaging system, wherein the detection mechanism measures light. The light source can be ambient light (e.g., from a natural source), light from an external artificial source, light from a light emitting element arranged within the system, a combination thereof, a secondary measurement system, such as a light-based remote sensing system (e.g., LIDAR, emitting light at about 10 micrometers to 250 nm), or any other suitable light source. The light source preferably emits/applies a light wave having a frequency of interest (e.g., a light frequency that is indicative of whether the plant expresses a phenotype of interest) to the plant, while the sensor preferably measures the light reflected by the plant. In one example of the system, the light source emits a broad spectrum of light, wherein a filter can be applied to the light source to limit the incident light on the plant to a predetermined light spectrum. In a second example of the system, the light source emits a broad spectrum of light, wherein a sensor is only sensitive to the frequency or interest. In a third example of the system, the light source emits a limited range of frequencies (e.g., the frequency or frequencies of interest), and the sensor is sensitive to the emitted range of frequencies. In a fourth example of the system, the light source emits a broad spectrum of light, wherein the plant-reflected light is filtered before reaching the sensor. In a fifth example of the system, the light source includes ambient light, wherein the ambient light is filtered, augmented (e.g., by auxiliary light sources), or otherwise adjusted to facilitate measurement by the sensor. However, any combination of the aforementioned examples or any other suitable method can be used to measure the visual characteristics of the plant.

In another variation of the system, the detection mechanism includes an audio system. Audio systems preferably include an emitter and a receiver (e.g., transducer or microphone), wherein the emitter can emit an audio signal having a parameter of interest (e.g., wavelength, decibels, etc.).

In another variation of the system, the detection mechanism includes a haptic system. The haptic system preferably includes a force applicator and a force sensor, and functions to measure the turgidity of the plant. The force applicator preferably applies a predetermined amount of force to the plant, and the force sensor preferably measures the amount of resistive force. Examples of haptic system include a brush that is brushed along the plant as the system passes by the plant, a pneumatically driven system that extends to apply the force to the plant, or any other suitable haptic system.

In another variation of the system, the detection mechanism includes an electronic system. The electronic system or electromagnetic system preferably includes an emitter and a receiver, but can alternatively include a first and a second electrode. The electronic system can be used to measure the resistivity, conductivity, or other electrical parameter of the plant. Examples of electromagnetic systems include an MRI system, a multimeter, a resistometer, an ampmeter, an inductor coil, or any other suitable electromagnetic system. However, any other suitable detection mechanism can be used.

The audio, electromagnetic, or any other suitable data is preferably compiled into a 3-dimensional model, wherein the characteristics are preferably extracted from the model. Alternatively, the characteristics can be directly extracted from the raw audio/electromagnetic data.

The detection mechanism preferably includes one or more plant morphology sensors 210 that functions to measure a morphology measurement 211, which can be plant data indicative of plant geometry. Examples of plant morphological data include plant or plant feature shape, size (e.g., based on a 2-D projection), profile, 3D geometry, root structure, shoot system structure, reproductive organ structure (e.g., corn tassel geometry), location in a geographic area, position within a 2-dimensional or 3-dimensional space, or any other suitable morphological data. In a specific example, the morphological and/or physiological measurements are compiled into a 2-dimensional or 3-dimensional virtual model 202. The plant morphology sensor 210 can additionally function to measure plant data indicative of plant positioning (e.g., arrangement, orientation, etc.) within the geographic field. Examples of plant position data include the plant distance from the sensor, plant distance from a physical marker embedded within the substrate or located on the system, or any other suitable plant position data. The plant morphology sensor measurements 211 can additionally be used to determine the morphology of any other suitable subject within the field of view (e.g., substrate features, size and shape of insects or other parasites, etc.).

The plant morphology sensor 210 is preferably oriented with the respective field of view directed toward the substrate, along a gravitational vector, but can alternatively be oriented with the field of view directed at a non-zero angle relative to the gravitational vector (e.g., oriented with the field of view directed along a normal vector to the gravitational vector, oriented with the field of view oriented 20 degrees from the substrate plane, etc.), arranged relative to the support base, or arranged in any other suitable position. The plant morphology sensor is preferably arranged above the plant, with the plant morphology sensor height greater than an estimated, actual, or measured plant height, such that the plant is arranged between the plant morphology sensor and the substrate during plant morphology sensor operation. However, the plant morphology sensor can alternatively be arranged beside the plant or arranged in any other suitable position.

The plant morphology sensor 210 is preferably an optical sensor, but can alternatively be any other suitable sensor. The plant morphology sensor is preferably a range imaging system, but can alternatively be an image sensing system (e.g., camera system) or any other suitable system. The plant morphology sensor can be statically mounted to the support, translatably mounted to the support, rotatably mounted to the support, or otherwise mounted to the support. Examples of the plant morphology sensor include a monocular camera (e.g., CCD or CMOS camera), stereo camera pair, multi-view system (e.g., with overlapping fields of view, a 3-view system, etc.), a range imaging system such as a LIDAR system, a time of flight system, a laser scanner, a projected light system (e.g., a system that determines the shape or dimensions of a plant by projecting a light pattern onto the plant and detecting the deformations in the reflected light), X-rays (e.g., CT scan), or any other suitable sensor. The laser scanner can include an emitter emitting a point or linear beam of light, paired with a receiver oriented across emitter with the subject configured to be arranged therebetween, wherein scanner measures sequential segments of the plant profile as the system translates relative to the plant (e.g., as the system translates along the geographic area). The stereo camera or multi-view system preferably capture two or more images having overlapping fields of view, but can alternatively have disparate fields of view. However, the system can include any other suitable plant morphology sensor.

The detection mechanism 200 preferably additionally includes a plant physiology sensor (vegetative parameter sensor) 220 that functions to measure a physiology measurement 221, which can include or provide plant parameters indicative of the plant physiology. The plant physiology sensor 220 can additionally function to measure ambient environment parameters. The plant physiology sensor preferably measures the signal across a 2-dimensional space, but can alternatively measure the signal across a 3-dimensional space or across any other suitable dimension. The plant physiology sensor is preferably used to create a 2-dimensional measurement of the subject, but can alternatively be used to create a 3-dimensional measurement or any other suitable measurement for the subject.

Examples of plant or ambient environment parameters that are measured can include optical parameters (e.g., visible wavelengths or color, non-visible wavelengths such as infrared, saturation, intensity, combination of wavelengths, etc.), aural parameters, electrical parameters (e.g., resistivity, conductance, etc.), chemical parameters, or any other suitable parameter or the plant or ambient environment. The measured parameter values can be subsequently used to calculate the plant indices, ambient environment indices, or any other suitable index. The index value for a plant is preferably determined based on measurements of the plant. One or more indices can additionally be determined for a plurality of plants. The index for the plurality of plants can be determined based on a measurement of the set of the plants (e.g., from a sensor having including all the plants in the field of view), or can be determined from the aggregate index values for each plant of the set. However, the indices can be otherwise determined.

The plant physiology sensor 220 is preferably substantially co-localized with the plant morphology sensor, such that the plant physiology sensor field of view overlaps or is the same as the plant morphology sensor field of view (e.g., within a predetermined error threshold). However, the plant physiology sensor can be arranged with the field of view perpendicular the plant morphology sensor field of view, or arranged in any other suitable position. The plant physiology sensor is preferably oriented with the respective field of view directed toward the substrate, along a gravitational vector, but can alternatively be oriented in any other suitable position. The plant physiology sensor is preferably arranged at a height greater than an estimated, actual, or measured plant height, such that the plant is arranged between the plant physiology sensor and the substrate during plant physiology sensor operation. However, the plant physiology sensor can alternatively be arranged beside the plant or arranged in any other suitable position.

The measuring area (e.g., field of view) of the plant physiology sensor is preferably fixed relative to the measuring area of the plant geometry sensor (e.g., statically coupled to the plant morphology sensor). Alternatively, the position of the plant physiology sensor can be fixed relative to (e.g., statically coupled to) the position of the geometry sensor. Alternatively, the plant physiology sensor can move relative to the geometry sensor. In this variation, the system can track the position (e.g., lateral position, longitudinal position, angle, etc.) of the plant physiology sensor and/or geometry sensor relative to a reference point on the system.

The system can include one or more plant physiology sensors. The plant physiology sensor can include a multispectral camera, a color camera (e.g., a RGB camera) such as a charge coupled device (CCD) or a camera including a CMOS sensor, a hyperspectral camera, an ultraspectral camera, a time of flight camera, a LIDAR system, an active light system (e.g., wherein a light, such as an IR LED, is pulsed and directed at the subject and the reflectance difference measured by a sensor, such as an IR sensor), thermal sensor, infra-red imaging sensor, or any other suitable imaging system. The multispectral cameras are preferably narrow-band multispectral cameras (e.g., a camera including a filter that measures wavelengths within a predetermined range of a given wavelength, such as within ±5 nm, ±2 nm, ±15 nm, wavelengths within a full width half maximum of the reflectance curve, or any other suitable range of a given wavelength), but can alternatively be wide band multispectral cameras or be any other suitable multispectral camera. In some variants, narrow band multispectral cameras can be preferable in measuring specific plant parameters of interest in enabling higher resolution measurements of the wavelengths of interest. The multispectral camera can record measurements at the 550 nm band, 650 nm band, 670 nm band, 700 nm band, 800 nm band, 900 nm band, 970 nm band, or any at any other suitable wavelength.

The system 100 can additionally include one or more ambient environment sensors 400. The ambient environment sensors 400 function to measure parameters of the ambient environment surrounding the subject of interest (e.g., the plant), which can subsequently be used to adjust the calculated plant indices. Ambient environment sensors can include a light sensor (e.g., a photosensor, an ambient light sensor, an artificial light sensor), a temperature sensor (e.g., for measuring the temperature of the emergent layer, canopy, understory, floor, or other portion of the plant), a humidity sensor, a conductivity sensor, a wind velocity sensor, a pressure sensor (e.g., barometer), a seismograph, a moisture sensor, a pH sensor, an ion meter, a clock, or any other suitable sensor.

The system can additionally include one or more location sensors, such as a GPS system, cell tower triangulation system, or any other suitable location system. The system can additionally include one or more position sensors, such as an accelerometer, gyroscope, or any other suitable position sensor. The position sensor measurements can be subsequently used to correct the measurements for detection mechanism 200 rotation. The system can additionally include a processor that processes the signals to identify individual plants (e.g., using the methods described in U.S. application '320, but alternatively any other suitable method). The processor can additionally process the signals to extract plant characteristics. Alternatively, the signals stored by the storage mechanism can be analyzed after the system has been passed over the plant field portion by a remote (e.g., off-system) processor.

The support 300 of the system functions to retain the detection mechanism position relative to the subject of interest (e.g., plant). The support can additionally function to retain the relative positions of multiple detection mechanism, translate the detection mechanism and computing system within the geographic area, or perform any other suitable function. The support is preferably a mounting base, but can alternatively be a housing mechanically protecting the sensors or be any other suitable sensor. The support preferably includes a drive axis 301, wherein the support traverses along a vector parallel to the drive axis. The support preferably additionally includes a base 320 that functions to support the system on the substrate. The base preferably defines a base plane, wherein the base plane is preferably parallel to the plane intersecting the points of base contact with the substrate. The base can additionally define an aperture extending along the drive axis that permits the support to travel over a plant (plant aperture) 302. The aperture 302 is preferably fixed at a predetermined height, but can alternatively have an adjustable height or have any other suitable height. The aperture is preferably the width of a crop row, but can alternatively have any suitable width.

The support can additionally include an extension member 340 that functions to retain the detection mechanism(s) a predetermined distance away from the base. The extension member preferably has a fixed length, but can alternatively have an adjustable length (e.g., be a telescoping arm, a pneumatic arm, etc.). The extension member is preferably statically coupled to the support base, but can alternatively actuate relative to the support base. The extension member preferably supports one or more detection mechanisms in a position outside the base perimeter, but can alternatively support the detection mechanisms in a position within the base perimeter, or support the detection mechanisms in any other suitable position. The detection mechanism 200 is preferably coupled to an end of the extension member 340, distal the base, but can alternatively be coupled along the length of the extension member, along a portion of the extension member, along a portion of the base, or along any other suitable portion of the support. In one variation wherein the detection mechanism is mounted to the base, the detection mechanism can be oriented toward the opposing side of the base, across the plant aperture defined through the base. The opposing side of the base can additionally include a marker, more preferably an optical marker, wherein the detection mechanism is preferably oriented with the marker within the detection mechanism field of view. The marker can function as a reference for the position, size, color, or any other suitable plant parameter.

The extension member and/or base preferably additionally defines a translucent window 321 that permits ambient light propagation therethrough. The translucent window can be an aperture, an aperture covered by a transparent or translucent covering (e.g., glass, frosted glass, colored glass, etc.), or any other suitable translucent window. In one variation, the support is an open box with a frame structure, wherein the translucent window is defined between the frame of the box.

The computing system 600 of the system functions to determine the plant indices based on the detection mechanism measurements. The computing mechanism can be a computing system, controller, PCB, device (e.g., a smartphone, tablet, laptop, etc.), or any other suitable computing system. The computing system is preferably configured to perform the plant index determination method, but can alternatively perform any other suitable method. The computing system is preferably arranged on the system, but can alternatively be remote from the system.

The system can additionally include a server system, remote from the field, that functions to receive the data from the system, store the received data, and/or process the received data. The data can include measurements, such as plant data and environmental data, extracted characteristics (e.g., derived data), such as plant characteristics and environment characteristics, treatment history, such as treatment history for an individual plant and treatment history for a plant field portion, or any other suitable data. In one variation of the method, the raw data is preferably transferred to the remote processing system 601, wherein the remote processing system processes the data into higher-level data. In another variation of the method, the raw data is compressed by the system before transmission to the remote processing system 601. The data can be received from the system in real time, after each session, or at any other suitable frequency. The data can be stored in the remote server system in a digital plant catalogue for each plant, for each plant genotype, for each plant field portion, or at any other suitable granularity. The data for each plant, genotype, or field portion is preferably associated with a location (e.g., received from the system identifying the location at which each measurement was taken), but can alternatively or additionally be associated with a plant, genotype, or field portion identifier. The data can be processed by the processor system to identify plants expressing a desired phenotype, identify plant genotypes and management practices that optimize for a desired result (e.g., yield, fruit characteristic, etc.), compute the correlation between observed traits and management practices or environmental conditions, generate future treatments, predict population responses, predict ideal harvest times (e.g., to maximize yield), or processed to obtain any other suitable information. The remote processing system can additionally receive and use data from secondary sources, such as a second database, in processing the data. For example, the remote processing system can access weather predictions in determining future plant treatments. The server system can additionally remotely adjust the operation of the system. For example, the server system can receive measurements from a first sensor in the plant field or a neighboring plant field (e.g., ambient lighting data due to cloud cover) and send adjustment instructions to the system based on the measurements, wherein the system can adjust the detection mechanism 200 to accommodate for the sensor measurement (e.g., adjust lighting intensity or renormalize recorded images).

The system can additionally include a storage mechanism functions to record the measured signals, and can be any type of digital or analog memory. The signals are preferably images, but can alternatively be a series of measurements, wherein each image or measurement is preferably associated with a timestamp (e.g., relative timestamp or global timestamp), and can additionally be associated with a location (e.g., relative location or global location), wherein the system can include a clock and a location mechanism, respectively.

Figure 2:
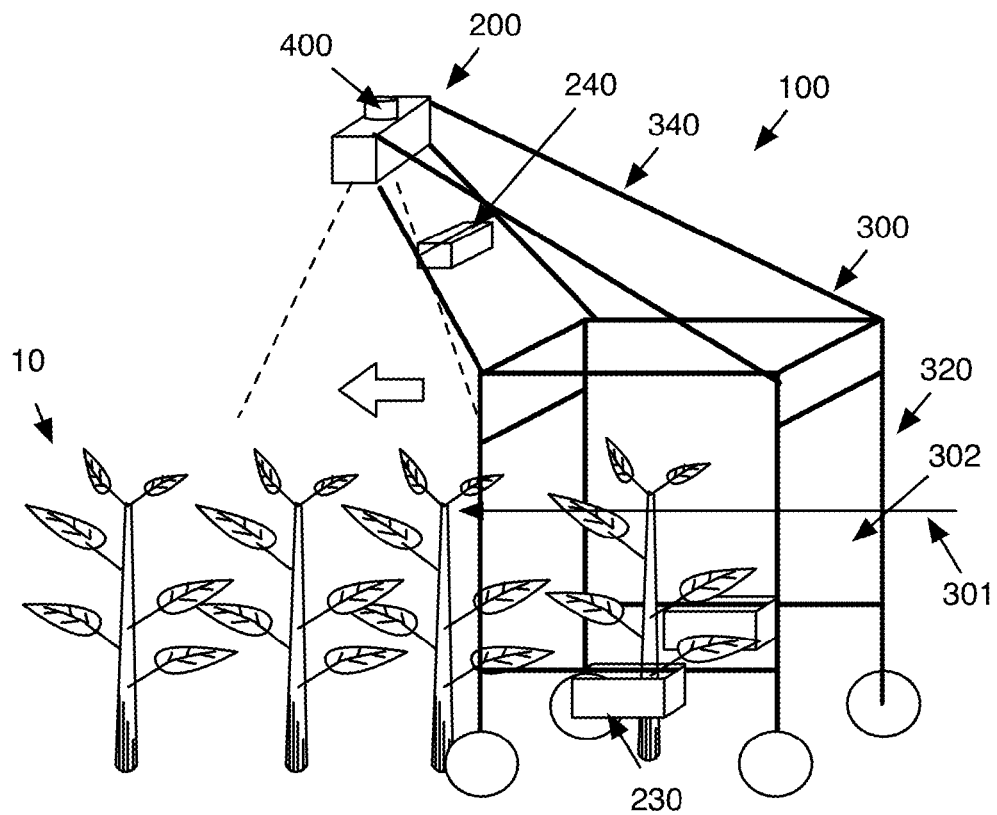
FIG. 2 is a schematic representation of a specific variation of the system in operation.

In one example as shown in FIG. 2, the system includes a morphology sensor, a physiology sensor, a support, and a computing system configured to receive measurements from the morphology sensor and physiology sensor, determine a set of plant pixels 222 within the physiology measurement based on the morphology sensor, and determine a plant index based on the set of plant pixels. The support preferably includes a base, wherein the base includes a first, second, third, and fourth adjacent leg, with the first leg adjacent the fourth leg. However, the base can include any other suitable number of legs. The legs are preferably fixed-length, but can alternatively have adjustable lengths (e.g., telescoping, pneumatic, etc.) or any other suitable configuration. The legs preferably terminate in a substrate coupling mechanism 350, which are preferably wheels but can alternatively be any other suitable substrate coupling mechanism. The substrate coupling mechanism preferably includes a base-substrate coupling point, but can alternatively include any other suitable reference point. The base can additionally include a first crossbeam or truss connecting the first and second legs, and a second crossbeam or truss connecting the third and fourth legs. The first and second crossbeams are preferably parallel the drive axis, but can alternatively be perpendicular or at an angle to the drive axis. The base can additionally include a third crossbeam connecting the second and third legs and a fourth crossbeam connecting the first and fourth legs. The third and fourth crossbeams are preferably arranged the aperture height from the ends of the third and fourth crossbeams configured to couple to the substrate, wherein the third and fourth crossbeams preferably cooperatively define the plant aperture with the second, third, first, and fourth legs, respectively. However, the base and plant aperture can be defined in any other suitable manner. In one specific example, a system configured to measure corn parameters includes a plant aperture at least 1.5 m in height, as measured from the point of base contact with the ground (e.g., base-substrate coupling point) to the third and fourth crossbeams. However, the plant aperture can be approximately 1.8 m in height (e.g., within a threshold distance), 3 m in height, 3 cm in height, or have any other suitable dimensions. The support preferably additionally includes an extension member mounted to the base proximal the third and fourth crossbeams.

Figure 3:
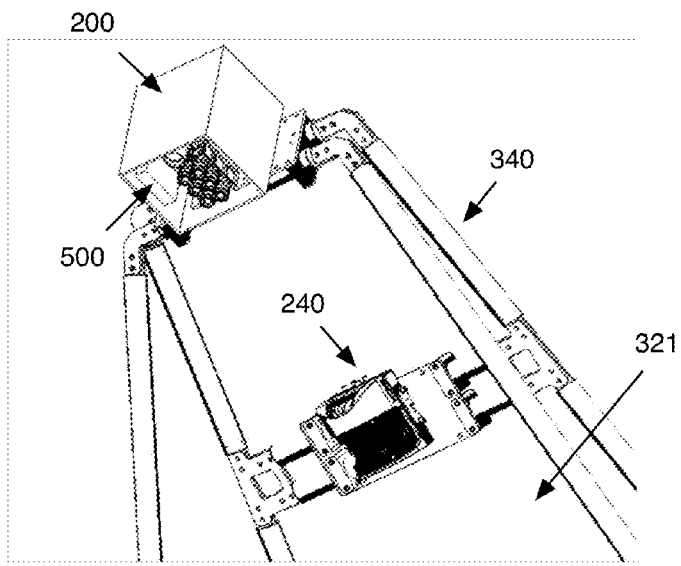
FIG. 3 is a schematic representation of a variation of the detection mechanism and extension member.

The morphology sensor and physiology sensor are preferably mounted to an end of the extension member distal the base, as shown in FIG. 3. The extension member preferably retains the morphology sensor and physiology sensor outside the volume normal the base perimeter, but can alternatively retain the morphology sensor and physiology sensor within the volume normal the base perimeter. The extension member is preferably statically mounted to the base, but can alternatively be movably mounted to the base. The extension member preferably retains the morphology sensor and physiology sensor a predetermined distance away from the base plane or substrate. In one specific example, a system configured to measure corn parameters includes an extension member that retains the morphology sensor and physiology sensor at least 2 meters from the substrate coupling mechanism, but can alternatively retain the sensors 1 meter from the substrate coupling mechanism, 5 meters from the substrate coupling mechanism, or any suitable distance from the substrate coupling mechanism.

The morphology sensor and physiology sensor are preferably oriented toward the base plane, more preferably oriented along a gravitational vector, such that the fields of view of the morphology sensor and physiology sensor encompass an area adjacent or encircled by the base. The morphology sensor and physiology sensor are preferably arranged such that the respective fields of view at least partially overlap (e.g., 10% overlap, 50% overlap, 90% overlap, etc.), if not entirely overlap a geographic area.

Figure 4:
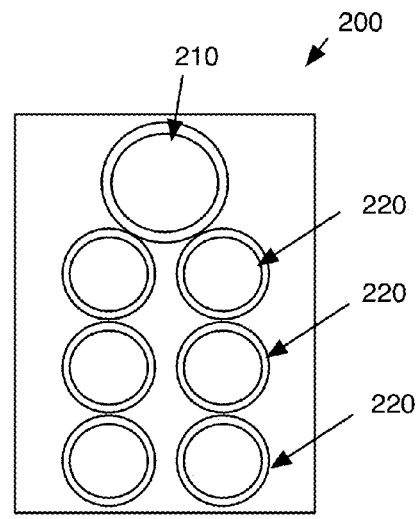
FIG. 4 is a schematic representation of a variation of the detection mechanism.
Figure 5:
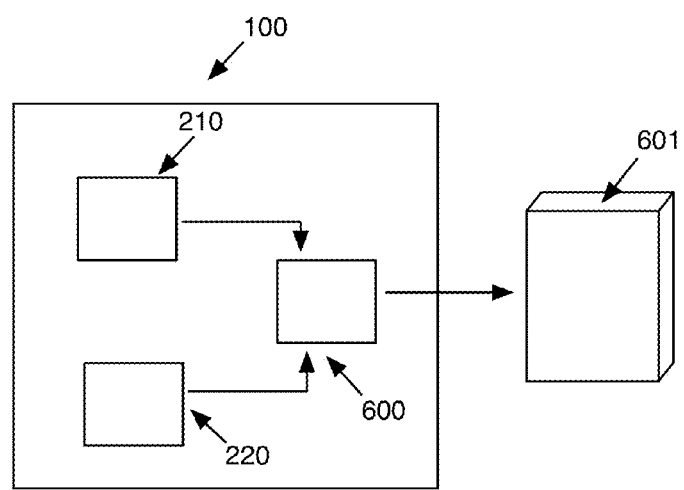
FIG. 5 is a schematic representation of a variation of the data transfer paths of the system.

The morphology sensor preferably includes a color camera (e.g., RGB camera), wherein the measurement is used to segment the plant (e.g., identify pixels associated with the plant). However, the morphology sensor can be any other suitable sensor. The physiology sensor is preferably a narrow-band multispectral sensor, but can be any other suitable sensor. More preferably, the system includes a set of physiology sensors, wherein the set of physiology sensors are preferably narrow-band multispectral sensors, but can additionally or alternatively include thermal cameras or any other suitable sensor. The narrow-band multispectral sensors are preferably arranged in an array, as shown in FIG. 4, but can alternatively be arranged in a circle, in a sphere, or in any other suitable configuration. In one variation, the system includes five monochrome cameras including optical bandpass filters that cooperatively measure both visible and near-IR wavelengths. In a specific example, the set of physiological cameras include a 550 nm band multispectral sensor, a 650 nm band multispectral sensor, a 700 nm band multispectral sensor, an 800 nm band multispectral sensor, and a 900 nm band multispectral sensor. The set of physiological sensors can additionally include a thermal camera measuring light between the 8 micrometer to 12 micrometer wavelength range. In a specific variation, the system lacks a dedicated green (e.g., measuring a set of wavelengths between the 495-570 nm wavelength) sensor, and leverages the color sensor to measure signals in this wavelength. The system can additionally or alternatively include a dedicated sensor that measures a set of wavelengths in the 600 nm-1000 nm wavelength range, wherein the dedicated sensor measures light provided by the range-finder system (e.g., LIDAR system) in addition to light provided by an ambient light source. The morphology measurement and the physiological measurement are preferably concurrently recorded, but can alternatively be sequentially recorded (e.g., the morphology measurement recorded before the physiological measurement or vice versa), be recorded within a period of time of the other measurement (e.g., predetermined period of time, such as within 1 microsecond, 1 second, 1 minute, etc., or within a period of time determined based on the system velocity), or recorded at any other suitable time. In a specific example, the morphology sensor and set of physiology sensors are clustered in an array, wherein the array is oriented with the lenses directed toward the base plane or substrate. The array is preferably shielded from the ambient environment (e.g., light, wind, water, etc.), but can alternatively be exposed. In a specific example, this array functions to measure data indicative of growth parameters, such as projected leaf area, leaf area index NDVI, TCARI/OSAVI, water stress, nitrogen stress, nitrogen content or any other suitable growth parameters indicated by the canopy leaves (e.g., new leaves) of the system.

Figure 8:
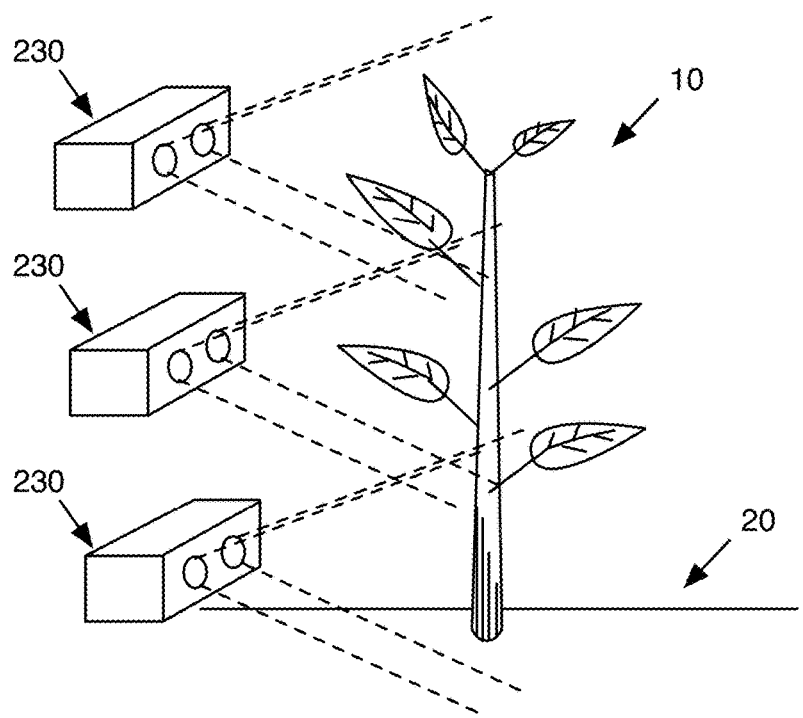
FIG. 8 is a schematic representation of various positions for the secondary morphology and/or physiology sensor.
Figure 9:
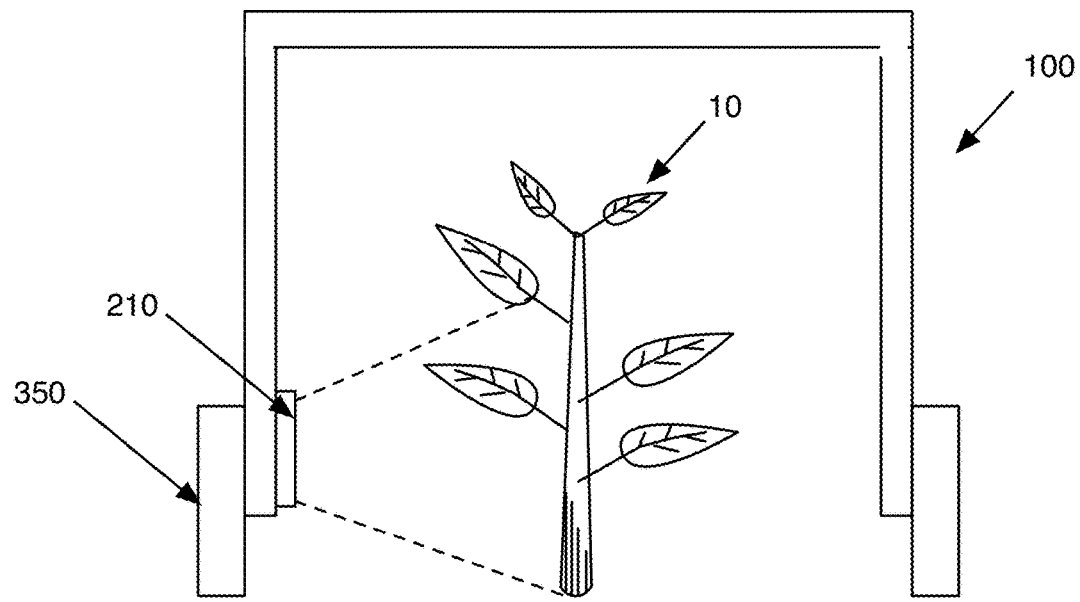
FIG. 9 is a schematic representation of a variation of the system including a secondary morphology sensor.

The system can additionally include a secondary morphology sensor 230 mounted to the base. The secondary morphology sensor is preferably a stereo camera that concurrently captures a first and second image having overlapping fields of view, but can alternatively be any other suitable sensor. The second morphology sensor is preferably mounted to the first or second crossbeam, but can alternatively be mounted along the length of a leg or mounted to any other suitable position. In a specific example, the system includes two secondary morphology sensors that function to measure the morphology of different parts of the plant. The first morphology sensor is preferably arranged between 40-60 cm away from the base-substrate coupling point and be configured to measure stalks, and the second morphology sensor arranged between 0.8-1.1 m away from the base-substrate coupling point can be configured to measure the geometry, number, or any other suitable parameter of fruits or reproductive organs (e.g., corn ears), an example of which is shown in FIG. 8, but the first and second secondary morphology sensors can alternatively be arranged at any other suitable height. In a specific example, the first secondary morphology sensor is oriented at the stem height, between the lowermost leaves and the substrate, such that the first secondary morphology sensor can measure the stand count (e.g., number of plants) within the geographic area, and the second secondary morphology sensor is oriented at fruit or reproductive organ height to measure data indicative of crop or seed yield. In another specific example, the system can include secondary morphology sensors mounted to the base at predetermined height intervals between the base-substrate coupling mechanism (e.g., wheel or wheel axle) and the first morphology sensor and/or physiology sensor, an example of which is shown in FIG. 9. Alternatively, a fixed number of secondary morphology sensors can be mounted at predetermined height ratios. Alternatively, the secondary morphology sensor heights can be determined based on the estimated or measured location of the lower leaves (e.g., wherein the secondary morphology sensor measures the stalks), the estimated or measured location of fruit, or determined based on any other suitable plant portion of interest.

The system can additionally include a tertiary morphology sensor 240 mounted to the extension member, between the first morphology sensor and the base. However, the tertiary morphology sensor can be mounted to the base (e.g., to the third or fourth crossbeam) or to any other suitable component of the system. The third morphology sensor is preferably a range finder system, such as a LIDAR system, which can function to measure plant height, but can alternatively be any other suitable sensor.

The system can additionally include a positioning system, such as a GPS system with RTK capability, triangulation system, or any other suitable system. The positioning system preferably records a geographic location measurement that is subsequently used to determine a geographic location (e.g., set of geographic coordinates) associated with the measurements taken by the morphology sensor and/or physiology sensor (e.g., based on timestamp). The positioning system is preferably fixed relative to the base, but can alternatively be fixed relative to the sensors, actuatable relative to the base, or coupled to the system in any other suitable manner. The geographic location of the measurements (e.g., the geographic location of each pixel of the measurements) are preferably determined based on the position of the sensor relative to the positioning system, the focal length, and/or the angle of view, but can alternatively be determined in any other suitable manner.

The system is preferably a passive system, and includes a photosensor, such as a pyranometer that functions to measure sunlight irradiance. The sunlight irradiance is preferably subsequently used to correct or otherwise adjust the signal measured by the physiometric sensor. The photosensor is preferably arranged on the extension member, on a surface distal the base, but can alternatively be arranged on the base (e.g., proximal the extension member mounting point, proximal the base-substrate coupling point, etc.), or arranged in any other suitable position. The photosensor is preferably arranged with a normal vector parallel a gravity vector or a normal vector to the base plane, but can alternatively be arranged at any other suitable angle relative to the base plane.

The system can additionally include an air temperature sensor which functions to measure the ambient temperature of the geographic area. The system can additionally include a humidity sensor for measuring the ambient humidity of the geographic area. The temperature sensor and humidity sensor are preferably arranged on the extension member, but can alternatively be arranged on the base (e.g., proximal the extension member mounting point, proximal the base-substrate coupling point, etc.), or arranged in any other suitable position. The ambient temperature and humidity measurements can subsequently be used to normalize the canopy temperature, as measured by the thermal camera.

However, the system can include any suitable combination of any of the aforementioned components.

2. Method.

Figure 6:
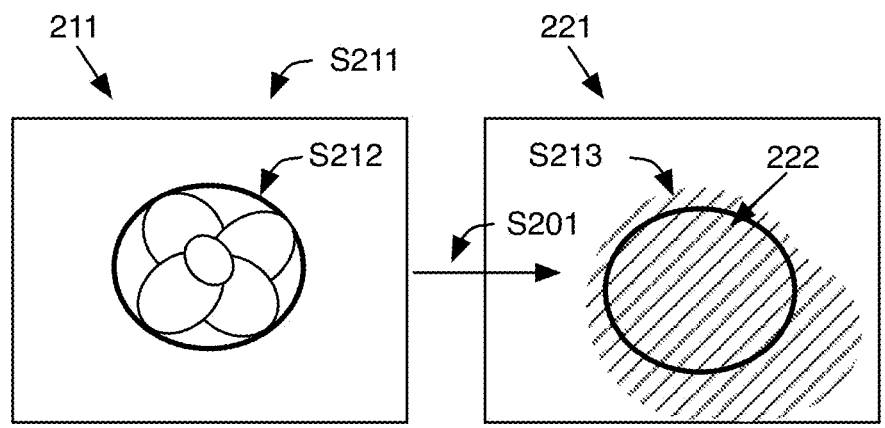
FIG. 6 is a schematic representation of identifying plant pixels within the physiological measurement based on a morphological measurement having a similar field of view.

As shown in FIG. 6, the method for index determination includes receiving a physiology measurement from the plant physiology sensor S100 and determining a plant index based on the physiology measurement S200. The method functions to determine plant index values for each of a plurality of plants, but can alternatively or additionally determine one or more plant index values for the geographic area or portion thereof. The method is preferably performed by the system described above, more preferably the computing system of the system described above, but can alternatively be performed by any other suitable system.

The method is preferably performed for each plant before the method is repeated for a second plant within the geographic area. Alternatively, separate steps of a first and second method iteration can be concurrently or substantially concurrently performed for a first and second plant, respectively. All steps of the method are preferably performed for a plant within a time window (e.g., within 5 minutes, within 1 minute, within 10 seconds, etc.), but can alternatively be performed asynchronously or outside of the time window. The second method iteration for a second plant within the geographic area is preferably performed within a second time window of the first method iteration for the first plant, wherein the second time window is preferably determined by the system velocity and spacing between the first and second plants within the geographic area. Alternatively, the second time window can be predetermined (e.g., be 5 minutes, 1 minute, 10 seconds, etc.). The method is preferably performed for the geographic area or for a plant at multiple time points (e.g., wherein growth history can be determined from the record), but can alternatively be performed a single time. The method is preferably performed for multiple plants within the geographic area, but can alternatively be performed for a single plant. The plants are preferably in situ (e.g., in a plant field), but can alternatively be in vitro (e.g., wherein the plants are planted in pots) or in any other suitable environment.

The plant data or plant index values that are determined from the data corresponding to the plant location are preferably recorded as the plant characteristics for the plant. For example, plant characteristics extracted from the area of an image determined to be associated with the identified plant (e.g., within the plant boundaries) are preferably stored in association with the plant. Individual plants are preferably identified by the plant location in successive data collection sessions, as visual, tactile, and other physical characteristics of plants tend to vary over time. However, individual plants can be uniquely identified based on a characteristic that has a low variation rate, such as stalk or trunk markings. Alternatively, the locations of each individual plant can be pre-mapped, wherein the plant characteristics extracted from each image is correlated to the pre-mapped plant based on the data location.

Figure 10:
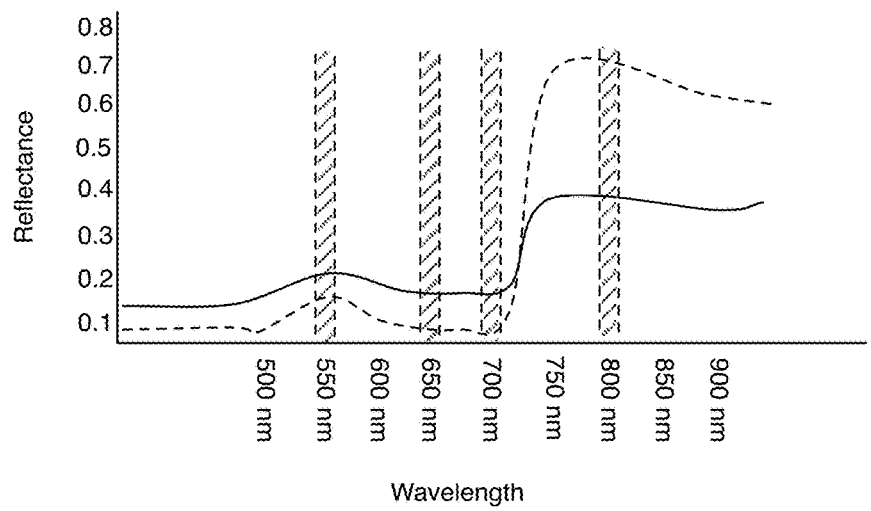
FIG. 10 is a schematic representation of example wavelengths that can be measured by the system.

Receiving a physiology measurement from the plant physiology sensor S100 functions to receive plant data indicative of plant physiology, which can subsequently be used to determine the plant index value. Receiving a physiology measurement additionally functions to record data of the phenotypic expressions of each individual plant within the plant field portion. The physiology measurement is preferably an optical measurement, such as the intensity of a wavelength, the on/off frequency, or any other suitable optical measurement, but can alternatively be an audio measurement (e.g., ultrasound, etc.), electric measurement (e.g., resistivity, conductance, etc.), haptic measurement, or any other suitable measurement. One or more physiology measurements can be received. As shown in FIG. 10, the physiology measurement is preferably a set of narrow-band multispectral measurements at the 550 nm band, 650 nm band, 670 nm band, 700 nm band, 800 nm band, 900 nm band, 970 nm band, between the 8,000 nm and 12,000 nm band, or any at any other suitable wavelength. However, the physiology measurement can be a set of wide-band multispectral measurements, or any other suitable measurement.

Determining the plant index S200 preferably includes determining the plant pixels from the physiological measurement S210 and processing the measurements to extract a plant parameter S220. Determining the set of plant pixels S210 functions to determine the plant pixels within the physiological measurement that correspond to the plant. This functions to distinguish signals from the ambient environment from signals from the plant. For example, both the substrate (soil) and plant include water; a top-down thermal image of a plant would include both measurements of the substrate and plant, which can be indistinguishable from the image itself. Furthermore, the signal associated with the plant area within the thermal image would be amplified or otherwise affected by the signal from the underlying substrate. In another example, both the plant of interest and background plants will reflect light in the wavelength of interest (e.g., in the 650 nm band), wherein the signals from the plant of interest and the background plants can be indistinguishable based on the image recording measurements in the 650 nm band alone.

The set of plant pixels preferably include pixels within the physiological measurement that are associated with the plant of interest. The pixels can identify the boundaries of each plant within the plant field portion, identify pixels within the boundaries, identify specific parts of the plant (e.g., plant leaves, stem, roots, flowers, fruits, apical meristem, apex, nodes, buds, etc., wherein the plant index can be subsequently determined for the specific plant part), or identify any other suitable plant portion or plant environment feature of interest.

In a first variation, the set of plant pixels can be identified from the physiology measurement. Identifying the set of plant pixels from the physiology measurement can include identifying a plant feature within the physiology measurement and determining the pixels surrounding or otherwise associated with the plant feature that are associated with the plant having the identified plant feature as the plant pixels. The plant feature can be identified by a measurement value different from measurement values of other or surrounding plant portions (e.g., corn silks can have a different green reflectivity than the surrounding leaves), a distinct measurement value pattern (e.g., corn silks can be identified by an area of low green reflectance surrounded by high green reflectance), or determined in any other suitable manner. Determining the plant pixels based on the plant feature can include estimating the area surrounding the plant feature that should be associated with the plant (e.g., based on machine learning techniques, historical measurements, etc.), identifying indicatory value gradients, or identifying the plant pixels in any other suitable manner.

Figure 14:
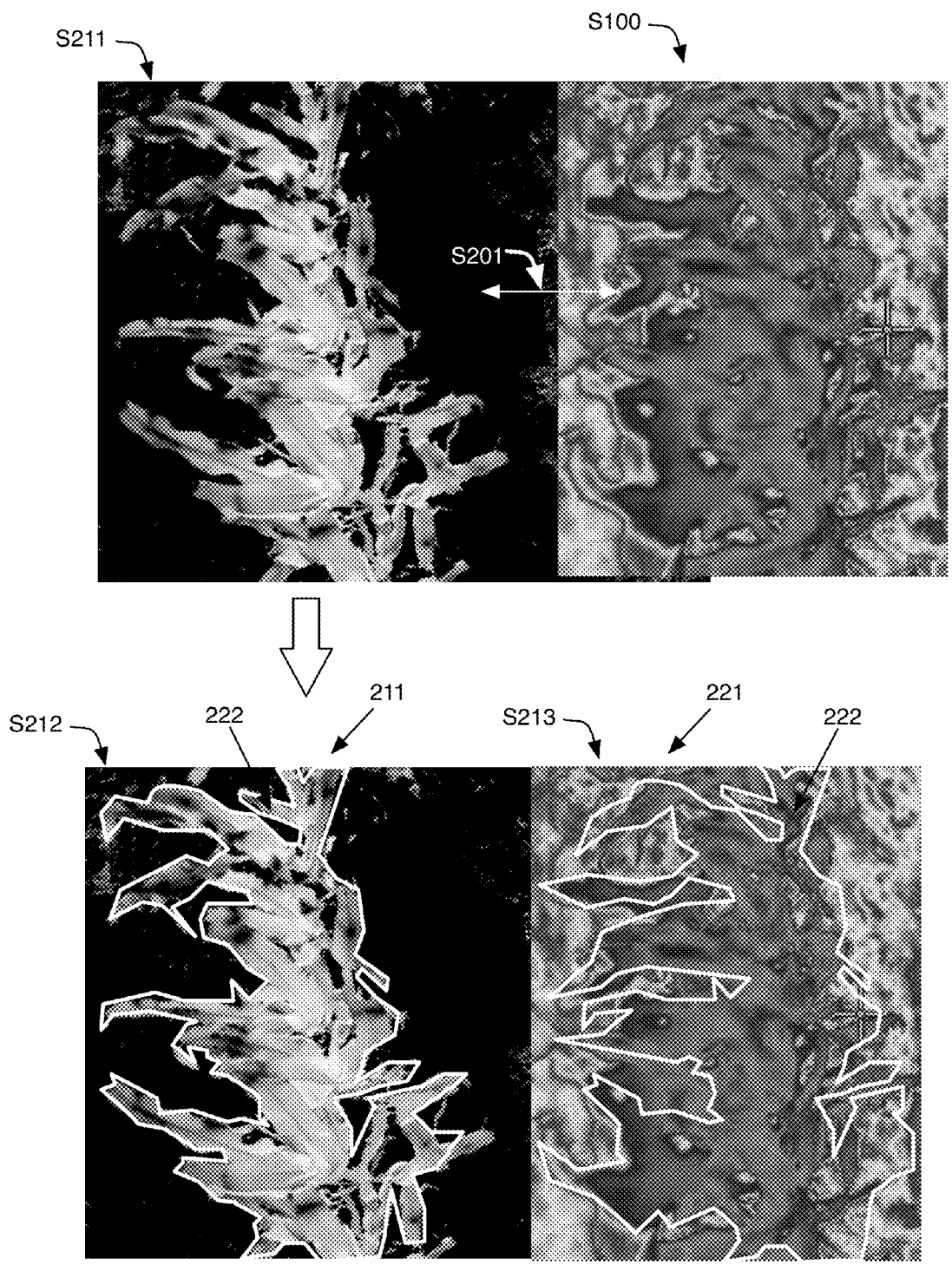
FIG. 14 is a specific example of identifying plant pixels within the physiological measurement based on a morphological measurement having a similar field of view, wherein the morphological measurement is a color measurement and the physiological measurement is a thermal measurement, and the determined plant index is the water stress of the plant.

In a second variation, identifying the set of plant pixels S210 can include receiving a morphology measurement from the plant morphology sensor S211, identifying a plant within the morphology measurement S212, and identifying the plant within the physiology measurement based on the subset of the morphology measurement that is associated with the identified plant S213, an example of which is shown in FIG. 14. In this variation, the plant geometry (e.g., the boundaries of the plant or plant portion of interest) is extracted with high resolution or reliability from the morphology measurement, then applied to the physiology measurement to identify the portions of the physiology measurement corresponding to the plant. This can increase the accuracy and/or precision of the plant index values extracted from the physiology measurement, because physiology measurements can lack the information to accurately and/or precisely identify plant boundaries.

Receiving a morphology measurement from the plant morphology sensor S211 functions to receive a measurement that can be used to determine the plant pixels. The plant pixels can be determined for the entire plant, a plant feature, or any other suitable plant portion. The plant pixels can be determined by identifying a plant boundary and determining the pixels within the boundary, by identifying a plant feature and identifying the pixels forming the image of the plant feature, by identifying pixels within the measurement having parameter values (e.g., color values) associated with the plant feature, or identified in any other suitable manner. The morphology measurement preferably has the same field of view as the physiology measurement, but can alternatively include a different field of view, an overlapping field of view, perpendicular fields of view, the same field of view from a different angle, a field of view directed to a different plant portion, or any other suitable field of view. In a specific example, the morphology sensor and physiology sensor are directed toward the same geographic location (e.g., latitude and longitude coordinates), and can be directed at the same or different altitudes. The morphology measurement is preferably taken concurrently with the physiology measurement to accommodate for plant movement (e.g., due to wind or robot-applied forces) between images, but can alternatively be taken before, after, or at any other suitable time. The morphology measurement can alternatively be taken a predetermined time before or after the physiology measurement, wherein the predetermined time duration can be pre-selected, dynamically determined (e.g., based on the system velocity), or determined in any other suitable manner. The morphology or physiology measurement recordation time can additionally or alternatively be determined based on an ambient environment parameter (e.g., wind speed). For example, the measurement can be recorded in response to the wind speed falling below a velocity threshold. Alternatively, the method of measurement recordation can be selected in response to the ambient environment parameter. For example, a shield can be extended to shield the plant from upstream wind in response to the wind velocity exceeding a threshold velocity. However, the measurements can be recorded at any other suitable time.

Receiving the morphology measurement can additionally include associating the morphology measurement with the physiology measurement S201. The morphology measurement is preferably associated with the physiology measurement that records data from the same or similar geographic area (e.g., the same plant, plant portion, etc.), but can alternatively be associated with a physiology measurement recording data from an area adjacent the area measured by the morphology measurement, or be associated with any other suitable physiology measurement. The morphology measurement (e.g., image) can be associated with the physiology measurement, a subset of the morphology measurement (e.g., a pixel of the image) can be associated with the entirety of the physiology measurement, a subset of the morphology measurement (e.g., a pixel of the image) can be associated with a subset of the physiology measurement, or any other suitable portion of the morphology measurement can be associated with any other suitable portion of the physiology measurement.

In a first variation, the morphology measurement can be associated with the physiology measurement through the respective timestamps. For example, a first stereoview image taken at a first time can be associated with a set of near-field multispectral sensor images taken at a second time, wherein the second time can be equal to, within a time duration of, or otherwise associated with the first timestamp.

In a second variation, the morphology measurement can be associated with the physiology measurement through odometry, based on the speed of the system and/or the distance travelled by the system. For example, the morphology sensor and physiology sensor can be separated by a known or estimated distance, wherein a morphology measurement, taken at a first timestamp, can be associated with a physiology measurement taken at a second timestamp, wherein the duration between the first and second timestamp is preferably equal to or approximately equal to the time taken to traverse a distance equal to the distance between the sensors. In other words, the measurements are preferably associated with other measurements measuring the same geographic area, as determined based on the system odometry. Alternatively, each system can have an independent odometry system, wherein the measurement taken by the sensor distal the direction of travel is correlated with a prior measurement taken by the other sensor in response to the distance travelled substantially matching the distance between the sensors.

In a third variation, the morphology measurement can be associated with the physiology measurement through a geographic location. In this variation, the morphology measurement and the physiology measurement each have an associated geographic location (first and second geographic location, respectively). The associated geographic locations are preferably determined based on the location of the position sensor (e.g., GPS) relative to the location of the respective sensor on the system, and can additionally be determined based on the direction of travel. In one variation, the pixels of the morphology measurement and physiology measurement are also each associated with a geographic location. The measurements sharing similar or the same geographic locations are preferably associated with each other. More preferably, the pixels sharing similar or the same geographic locations are associated with each other.

The measurements are preferably associated with a plant location as the data is collected, but can alternatively be associated with a timestamp (e.g., universal or relative, such as to a starting time) that is used to estimate the location at which the data was collected. The measurement location is preferably a global location (e.g., latitude and longitude coordinates, as measured by a GPS device), but can alternatively be a relative location (e.g., relative to a starting point) determined based on the timestamp and the recorded travel path of the system, be a relative location determined using triangulation, or be determined in any other suitable manner. The plant location is preferably determined from the measurement location, more preferably from the location of the measurement from which the plant was identified. In one variation of the method, the plant location is determined from image location, wherein the plant location is preferably the image location adjusted by the position of the plant in the image. In another variation of the method, the plant location can be identified by a visual or wireless identifier (e.g., QR code, bar code, text, RFID tag, etc.) that is added to the plant, the plot, the crop row, or to any other suitable location related to the plant. However, the plant location can be otherwise determined.

In a fourth variation, the morphology measurement can be associated with the physiology measurement through the field of view angle. For example, the morphology sensor and the physiology sensor are preferably directed at the same field of view, or from different angles at the same viewing area, such that measurements taken concurrently are correlated. In a specific example, the physiology sensor field of view can include the morphology sensor (or vice versa), such that any detected movement or offset of the viewed sensor can be detected and dynamically accounted for in the measurement processing.

Identifying a plant within the morphology measurement S212 functions to identify the portions of the morphology measurement that correspond to a plant. The identified morphology measurement portions are subsequently compared to the physiology measurement to identify portions of the physiology measurement that correspond to the plant. More preferably, identifying the plant within the morphology measurement includes identifying the pixels corresponding to the plant within the morphology measurement.

Identifying a plant within the morphology measurement preferably functions to identify an individual plant, more preferably the boundaries and/or area associated with the plant, but can alternatively identify a set of plants or any other suitable number of plants. Alternatively, identifying a plant includes identifying a plant feature. The plant feature that is preferably unique relative to the rest of the plant, such as a plant center, apical bud, solitary fruit, or any other suitable unique feature. However, any other suitable plant feature or portion, such as the stem, leaves, nodes, or any other suitable feature.

In one variation, identifying the plant includes segmenting the background from the foreground, wherein the plant is preferably within the foreground of the image. The morphology measurement is preferably segmented according to the method described in U.S. Application '320, but can alternatively be segmented in any other suitable manner. The image can be can be segmented based on color (e.g., intensity), focus (e.g., edge sharpness), or any other suitable image parameter.

In another variation, a unique plant feature (e.g., a singular plant feature that appears below a predetermined frequency on a plant) is identified within the morphology measurement, and secondary plant features connected to or adjacent the unique plant feature are identified. The secondary plant features are preferably traced to determine the extent of plant spread. The tertiary, quaternary, or any suitable number of linked plant features can additionally be determined in this manner from the unique plant feature. Whether the other plant features are identified can be determined based on the type of identified plant feature. For example, the method can include identifying a plant center, identifying primary leaves connected to the plant center, identifying secondary leaves adjacent to the primary leaves satisfying a predetermined parameter (e.g., estimated leaf angle), and identifying tertiary leaves adjacent the secondary leaves. The identified type of plant may be known to not include quaternary leaves, so any leaves adjacent the tertiary leaves may be considered leaves of another plant. The plant features can be identified using RANSAC algorithms for shape detection, shape fitting, surface curvature fitting, global fast point feature histogram, or any other suitable method.

In another variation, the plant pixels are determined based on a virtual model that is built from the morphology measurement, wherein the method additionally includes generating the virtual model S202. The virtual model 202 is preferably newly generated for each pass over the plant (e.g., for each morphology measurement of the plant), but can alternatively be updated based on each new morphology measurement for the plant. A virtual model can be created for the entire plant, a plant feature (e.g., the plant stem, reproductive systems or fruit, etc.), segment of the plant feature, or any other suitable portion of the plant. The virtual model can additionally or alternatively be created for the geographic area or a subset thereof (e.g., a virtual model of the plant field), wherein the virtual model can be formed from the virtual models of each measured plant in the field. The plant positions in the virtual field are preferably based on the distance between the plants in the geographic area, as determined by odometry or any other suitable distance determination method. Furthermore, growth models for the plant or a set of plants can be determined from the virtual models. Different virtual models for each plant, generated based on morphology measurements taken at different time points, can be aggregated into the growth model. The phenotypic data for the plant or plant portion can additionally be included to obtain a phenotypic growth model. However, any other suitable virtual model can be created.

In one specific variation, the virtual model 202 is determined using shape fitting techniques. However, the virtual model can be determined using edge detection, primal sketch, recognition by parts, edge matching, divide-and-conquer search, greyscale matching, gradient matching, histograms of receptive field responses, large modelbase learning, interpretation trees, pose consistency, pose clustering, invariance, geometric hashing, scale-invariant feature transform, speeded up robust features, genetic algorithms, or any other suitable technique. The shape fitting technique preferably includes identifying a feature of the plant portion of interest within the morphology measurement S203 and identifying a best-fit set of curves or spline that traces a border or main feature of the plant portion S204.

The method can additionally include fitting a shape 205 having a cross section similar to a known or estimated plant portion cross section to the morphology measurement S205, based on the spline. The method can additionally include selecting the shape or cross section to be fit to the set of curves based on the plant feature. For example, cylinders can be selected for the plant stem, a polymetric surface can be selected for a leaf, and an obloid or sphere can be selected for a fruit or reproductive organ (e.g., corn ear). The shape or cross section can be selected by a user, automatically selected (e.g., based on machine learning techniques), or otherwise selected.

The plant or plant portions of interest can be obstructed by other plant portions (e.g., leaves) of the same plant or adjacent plants. To accommodate for the obstruction, the set of curves 204 or shapes 205 are preferably fit to the visible portions of the plant portion (e.g., using shape inference methods), such that the obstructed portions are extrapolated, but can alternatively be otherwise fit to the plant portion. Examples of shape inference techniques include fitting Gaussian curves, caternary curves, piecewise linear curves, hyperbolic curves, elliptical curves, or any other suitable curves to the plant portion. By inferring the shape of the plant portion, the plant portion can be modeled using morphological images from a limited number of viewing angles. In another variation of the method, the obstructed plant portions are modeled by identifying a reference point (e.g., a plant feature, such as a stem, node, or leaf) from the morphological measurement, determining a location of the plant portion of interest relative to the reference point (e.g., retrieving the location from a historical measurement or model), generating a new virtual model of the plant portion including the reference point based on the new measurements, comparing the new virtual model to the historical model by aligning or otherwise matching the reference points, and associating the closest matching plant features in the new model with the plant features in the historical model (e.g., wherein the plant features can be corrected for estimated plant growth). In another variation of the method, an obstructed plant can be identified by identifying a reference plant within the new morphological measurement, determining a location of the reference plant within a historical model, determining a location of the plant relative to the reference plant within the historical model, generating a new virtual model of the plants within the geographical area including the reference plant based on the new measurements, comparing the new virtual model to the historical model by aligning or otherwise matching the reference plants, and associating the closest matching plants in the new model with the plants in the historical model (e.g., based on plant growth pattern, relative size, relative shape, relative position, relative orientation, etc.). However, obstructed plants or plant features can be otherwise identified.

The method can additionally include identifying one or more morphological parameter values for the plant feature, the entire plant, the plant interactions with neighboring plants, for a population of plants (e.g., across a portion or entirety of a plant field), or for any other suitable set of plant features or plants. The morphological parameter values can additionally or alternatively be determined by comparing the respective morphological parameter values for a first plant feature with a second plant feature, a first plant with a second plant, a first geographic area with a second geographic area, or any suitable combination thereof.

Examples of morphological parameter values for the plant feature can include the stem straightness, the leaf curl, the leaf area, the leaf height, the angle of the leaf junction with the stem, the leaf position on the plant or within a geographical volume, fruit geometry, fruit positioning relative to the stem, corn silk density, or any other suitable morphological parameter. Examples of morphological parameter values for the entire plant include the plant height, plant uniformity, plant straightness, or any other suitable parameter. Examples of morphological parameter values for plant interactions with neighboring plants (e.g., neighboring plant parameters) includes the distance between stalk-substrate junctions (e.g., the distance between stalks of adjacent plants), the distance between a plant feature of the plant and a plant feature of an adjacent plant (e.g., distance between a corn silk tassel to an adjacent corn ear or distance between a fruit and an adjacent plant stalk, etc.), the amount of overlap between adjacent plants (e.g., amount, distance, percentage, or any other suitable qualifier of adjacent leaf overlap or cover of the plant), or any other suitable morphological parameter. Examples of population parameter values include the spread of a characteristic (e.g., specific or range of parameter values) over the entirety or portion of the geographic area, determination of plant population uniformity (e.g., determination of the location, spread over time, etc. of a specific plant phenotype), population-wide changes over time (e.g., gradual tree lean across the population), or any other suitable population-level information.

Figure 11:
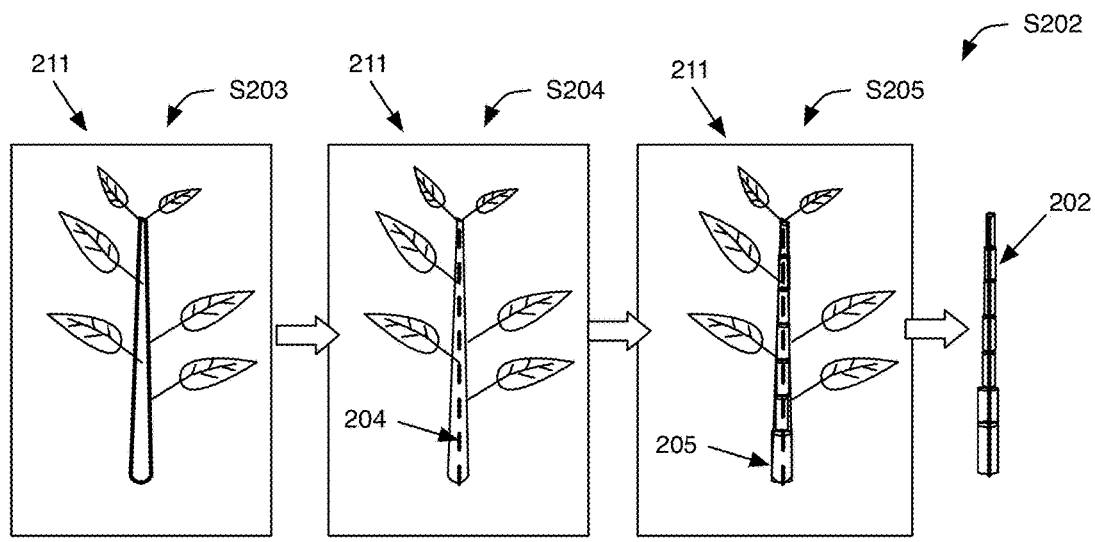
FIG. 11 is a schematic representation of an example of generating a 3-dimensional virtual model of a plant stem, including identifying the plant stem within the morphological measurement, identifying a set of best-fit curves indicative of a longitudinal axis of the stem, determining a set of best-fit cylinders for the plant stem based on the set of curves, and generating the virtual model based on the set of curves and cylinders.

In a first example as shown in FIG. 11, the method generates a 3-D model of a plant stem. Generating the model of the plant stem can include identifying a set of pixels (continuous, adjacent, or any other suitable pixel) indicative of the stem and fitting a set of splines (e.g., piecewise polynomial), curves, or other two-dimensional vectors (e.g., one or more) to the set of pixels indicative of the stem. The spline parameters, such as length, curvature, or any other suitable parameter, can be used to determine the stalk parameters. In a specific example, the curvature of the best-fit spline can be used to determine the stalk straightness, wherein curvatures above a threshold radius can be indicative of stalk breakage (e.g., lodging) and detected. However, the spline parameters can be otherwise used. Generating a model of the plant stem can additionally include fitting a set of cylinders based on the spline (e.g, to the spline, along the spline, etc.). The cylinders are preferably right cylinders, but can alternatively be any other suitable cylinder or shape. The method can additionally include adjusting the diameter of one or more cylinders to fit the stem in the image. The cylinder parameters (e.g., diameter, length etc.) are preferably used to determine stalk parameters. In a specific example, the cylinder diameter can be used to determine the stalk diameter, which can subsequently be used to determine stalk or plant biomass. The set of splines or cylinders can additionally be used to determine which plant features, such as leaves, fruits or other reproductive systems, or roots, are associated with the same plant. However, the stem can be otherwise modeled, and the model otherwise used.

Figure 12:
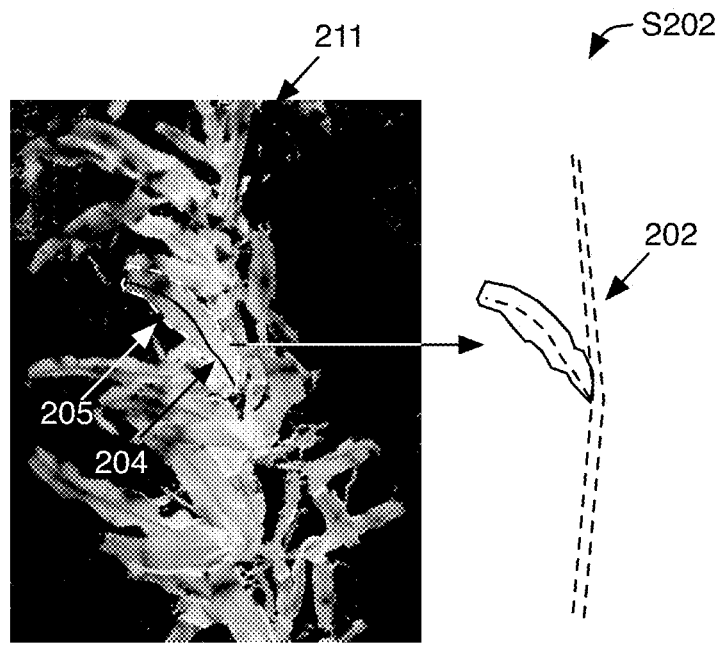
FIG. 12 is a schematic representation of an example of generating a 3-dimensional virtual model of a plant leaf, including identifying the plant leaf within the morphological measurement, identifying a set of best-fit curves indicative of a main leaf vein, determining a best-fit parametric surface for the leaf, and generating the virtual model based on the set of curves and surfaces.

In a second example as shown in FIG. 12, the method includes generating a 3-D model of a plant leaf. Generating the model of the plant leaf can include identifying a set of pixels (continuous, adjacent, or any other suitable pixel) indicative of the leaf, and fitting a set of parametric surfaces, splines, or other 2-dimensional or 3-dimensional surface or curve to the leaf. The curvature of the parametric surface preferably substantially matches the leaf curvature or curvature of a leaf feature within the morphological measurement, but can alternatively be different. In a specific example, the method can include identifying a main leaf vein or other longitudinal leaf feature, fitting a spline to the vein, and fitting a parametric surface to the spline. However, the parametric surface curvature can be otherwise determined. The edges of the parametric surface preferably substantially matches the leaf boundaries (e.g., wherein the leaf boundaries are determined by edge recognition or other techniques), but can alternatively be different. The vein spline and leaf area parametric surface can be determined from a single morphological measurement or multiple morphological measurements. The parametric surface and/or spline parameters can be extracted and used to determine leaf parameters. Examples of leaf parameters include the leaf roll, leaf curvature relative to the main vein or another leaf feature, the angle of the leaf relative to the stalk, leaf height change between the leaf-stem junction and the leaf curvature apex, leaf position and/or orientation relative to the stem or geographic location, or any other suitable leaf parameter. These leaf parameters can subsequently be used to determine plant indices, disease indicators (e.g., from leaf curl), or any other suitable plant information. However, the leaf can be otherwise modeled, and the model otherwise used.

Plant growth can be further determined from multiple measurements taken over a period of time, wherein a plant growth model can be determined for a plant feature, entire plant, plant population, or any other suitable set of plants based on the multiple measurements and associated with the respective measurement timestamp. The plant growth can be determined based on new leaf growth, wherein new leaves can be the leaves present in a subsequent virtual model that were not in a previous virtual model. Old leaves can additionally or alternatively be determined from this growth model. The old leaves can additionally or alternatively be determined based on the color, size, or any other suitable parameter. The growth model can additionally or alternatively be used to determine physiological process parameters, such as flowering time (e.g., based on the rate of new leaf growth).

Figure 13:
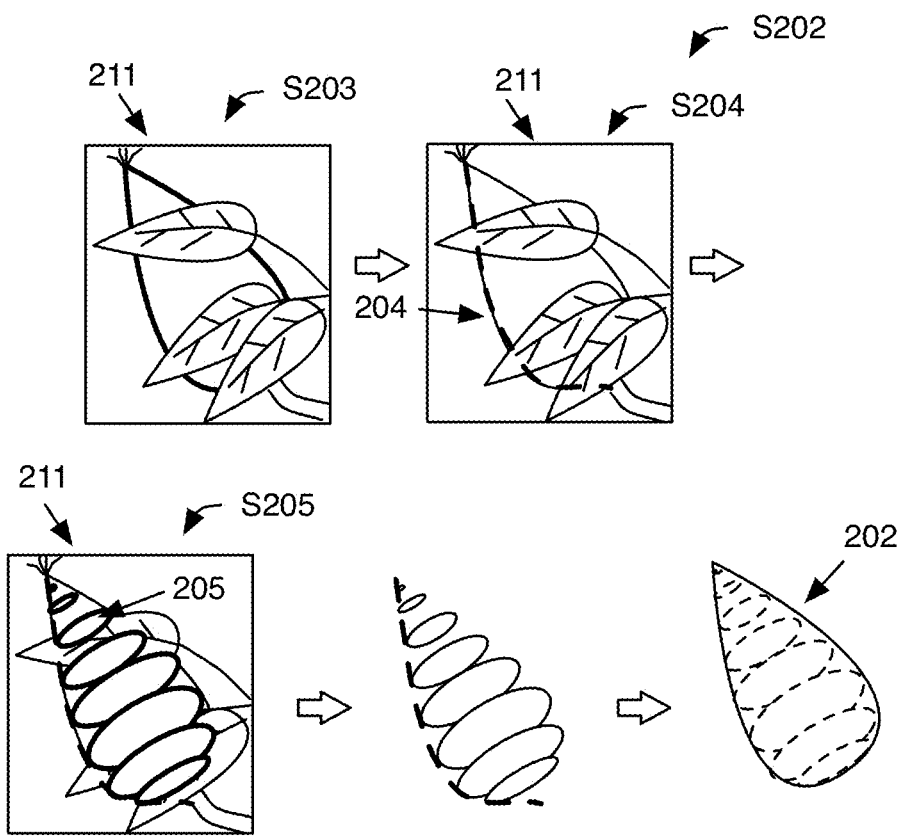
FIG. 13 is a schematic representation of an example of generating a 3-dimensional virtual model of a plant fruit, including identifying the plant fruit within the morphological measurement, identifying a set of best-fit curves indicative of a fruit border, determining a set of best-fit cross-sections having a predetermined shape for the fruit, and generating the virtual model based on the set of curves and cross-sections.

In a third example as shown in FIG. 13, the method includes generating a 3-D model of a fruit (e.g., a reproductive organ). Generating the model of the fruit can include identifying a set of pixels (continuous, adjacent, or any other suitable pixel) indicative of the fruit, and fitting a set of curves (e.g., a spline) to a portion of the fruit. The portion of the fruit that the line is fit to can be the border of the fruit, a longitudinal fruit feature (e.g., the line extending along a stone fruit exterior), or any other suitable portion of the fruit. The method can additionally include fitting a shape to the set of curves. The shape is preferably determined based on the type of fruit, but can alternatively be otherwise determined. Alternatively, a cross-section can be selected based on the type of fruit (e.g., a circular cross-section, an oblong cross-section, etc.), wherein the shape is formed from a set of cross-sections aligned with the spline along a cross-section perimeter, center point, or any other suitable cross-section portion. For example, a corn ear can be determined by fitting an spheroid to a spline defining the corn ear boundary. In another example, a corn ear can be determined by fitting a set of ellipses or circles perpendicular to the spline defining the corn ear boundary. The best-fit shape is preferably used to determine fruit volume or fruit proximity to a neighboring plant, but can alternatively be used to determine other fruit parameters. The best-fit spline can be used to determine fruit orientation relative to a stem, fruit length, or any other suitable fruit parameter. However, the fruit can be otherwise modeled, and the model otherwise used.

In a fourth example, the method includes generating a 3-D model of a plant feature (e.g., the tassels of the corn silk). Generating the model of the plant feature can include identifying a set of pixels (continuous, adjacent, or any other suitable pixel) indicative of the fruit, and fitting a set of curves (e.g., a set of splines) to the feature. For example, a set of curves can be fit to at least a subset of corn ear tassels. Parameters of the set of curves can be extracted and used to determine feature parameters. For example, the tassel color, volume (e.g., determined from the spatial distribution of the curves), uniformity, length (e.g., determined from the curve lengths), curvature (e.g., determined from the curve curvature), or any other suitable tassel geometry parameter can be extracted from the set of curves. The curves can be further used as a reference point to identify secondary plant features adjacent the first plant feature, or can be referenced against the parameters of the secondary plant features to extract morphological information. For example, the method can include determining the lean of the corn ear tassels (e.g., as determined by the curvature of the respective curves) relative to the angle of the adjacent corn ear leaves (e.g., as determined using a method described above). However, the plant features can be otherwise modeled.

However, any other suitable image processing technique can be used to segment the plant of interest from the background (e.g., soil or adjacent plants).

Identifying the plant within the physiology measurement based on the subset of the morphology measurement that is associated with the identified plant S213 functions to distinguish between the physiological signals corresponding to the plant, and the physiological signals corresponding to the background. In a first variation, both physiological and morphological information can be extracted from the same measurement (e.g., wherein the measurement can be a color stereo image).

In a second variation, the morphology measurement and the physiology measurement have the same field of view. In a first embodiment, the pixels corresponding to the plant pixels in the morphology measurement are assigned as the plant pixels of the physiology measurement. In one example, the physiology and morphology measurements are overlaid and the physiology pixels overlapping the morphology measurement plant pixels are determined. When the morphology measurement and the physiology measurement have similar (e.g., overlapping) fields of view, the pixel correlation can be adjusted by the offset between the morphology measurement field of view and the physiology measurement field of view. In a second embodiment, identifying the plant within the physiological measurement includes determining an identifier for one or more plant pixels of the morphological measurement and determining the pixels within the physiological measurement having the determined pixel identifiers. For example, the method can include determining the geographic location of the plant pixels of the morphological measurement and identifying the pixels of the physiological measurement associated with the identified geographic locations. However, morphology measurement pixels can be otherwise correlated with physiology measurement pixels when the morphology sensor and the physiology sensor have the same or similar fields of view.

Figure 7:
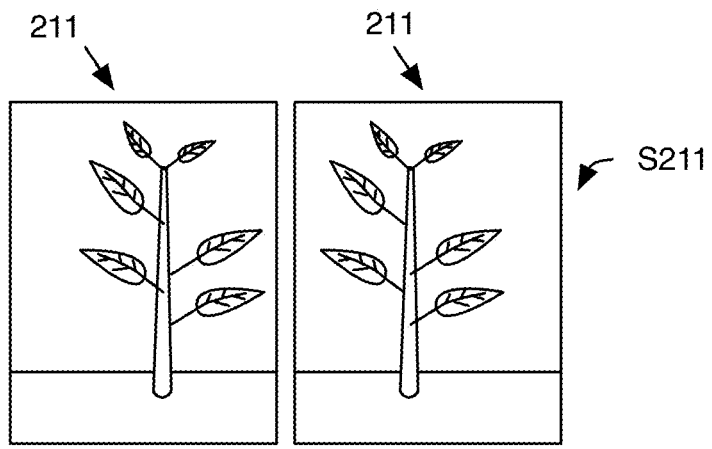
FIG. 7 is a schematic representation of identifying plant pixels within the physiological measurement based on a morphological measurement having a different field of view from the physiological sensor.
Figure 7:
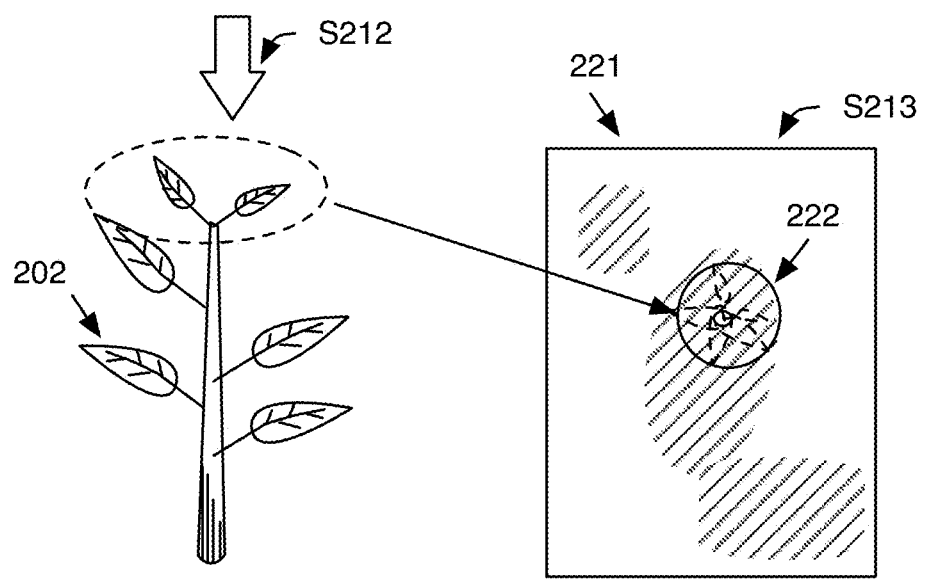
Figure 15:
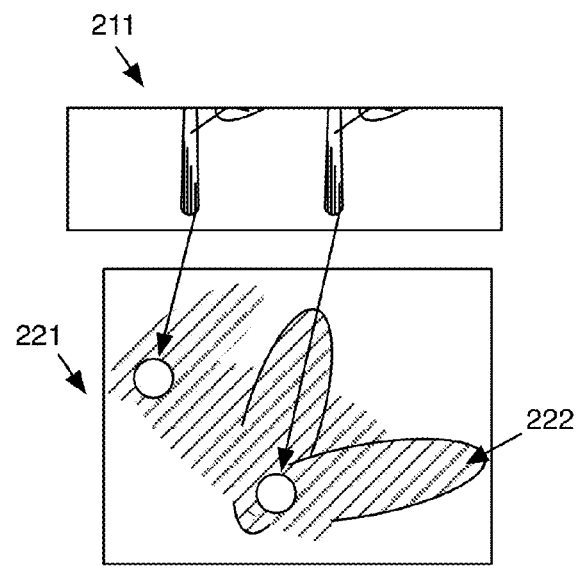
FIG. 15 is a specific example of using a first morphological measurement to distinguish between plants in a second morphological measurement having a different viewing angle.

In a third variation, the morphology measurement and the physiology measurement can have different fields of view, and can be directed at different plant portions. For example, the physiology sensor can be directed at the top of a plant (e.g., have a top-down view of the plant), while the morphology sensor can be directed at the side of the plant (e.g., at the stem). The method preferably includes identifying a first plant portion within the morphology measurement, identifying a set of geographic locations associated with the plant portion, determining a second set of geographic locations associated with the plant and with the physiological measurement, and identifying the pixels corresponding to the second set of geographic locations. The second set of geographic locations can be the same as the first set of geographic locations, or can be a different set of geographic locations. The second set of geographic locations can be estimated, calculated, or otherwise determined. The second set of geographic locations can be determined based on the first set of geographic locations, the portion of the plant identified (e.g., the stem, leaves, fruit, etc.), or based on any other suitable parameter. In one example, as shown in FIG. 7, the stem of the plant is identified in the morphological measurement, the growth direction of the stem is estimated or determined based on the morphological measurement (e.g., using region crawling), the set of geographic locations associated the canopy determined or estimated based on the geographic location(s) of the stem and the growth direction, and the pixels associated with the set of geographic locations identified within the physiological measurement. In another example, the stem of the plant is identified in the morphological measurement, a set of stem geographic locations is determined, the canopy spread is estimated (e.g., based on the morphological measurement values or secondary measurements), and the set of pixels associated with the estimated canopy spread about the set of stem geographic locations is identified within the physiological measurement. However, the set of plant pixels can be otherwise determined within the physiological measurement. In another example, the stem or other key identifying feature of the plant is identified in a first morphological measurement, a set of stem geographic locations is determined based on the first morphological measurement, and the set of stem geographic locations is used to estimate or determine the initiation point for plant identification in a second morphological measurement. The amount of overlap can additionally or alternatively be augmented with physiological measurement values (e.g., the overlapping portion is associated with a lower light intensity). This can be particularly useful when an adjacent plant obstructs the plant from view in the second morphological measurement, as shown in FIG. 15.

Figure 16:
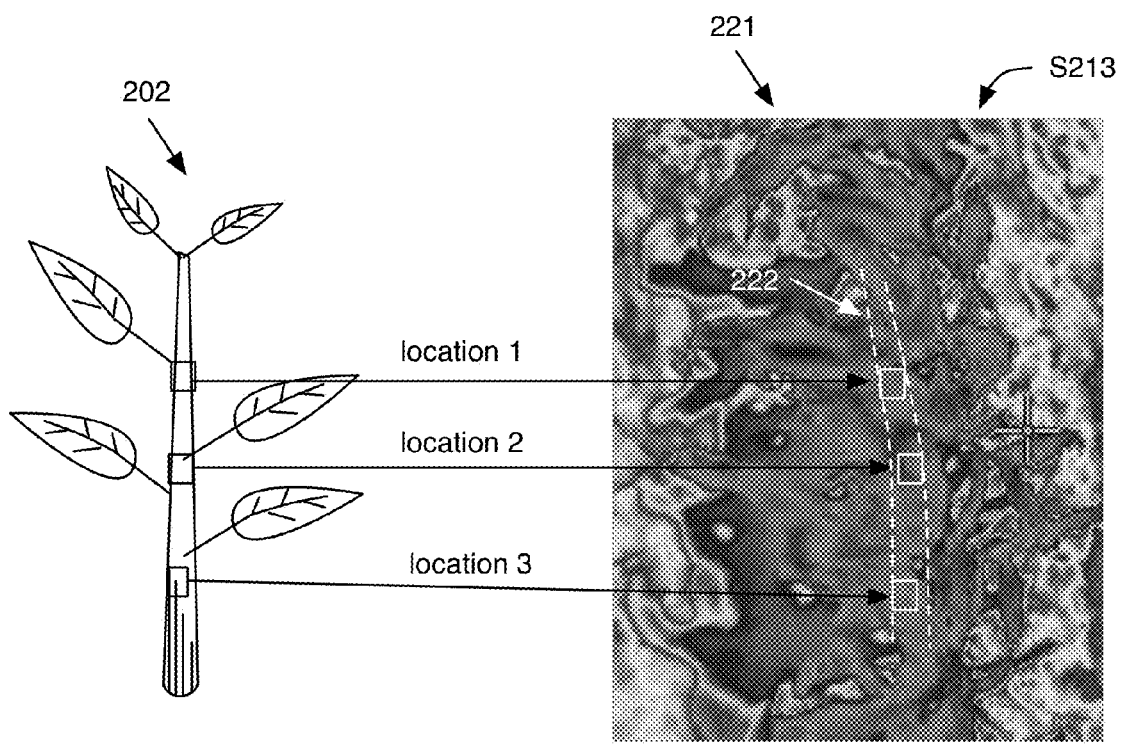
FIG. 16 is a schematic representation of a second variation of identifying the plant pixels in the physiological measurement using the 3-D virtual model, using geographic volumetric identifiers or geographic locations to correlate virtual model points with physiological measurement pixels.
Figure 17:
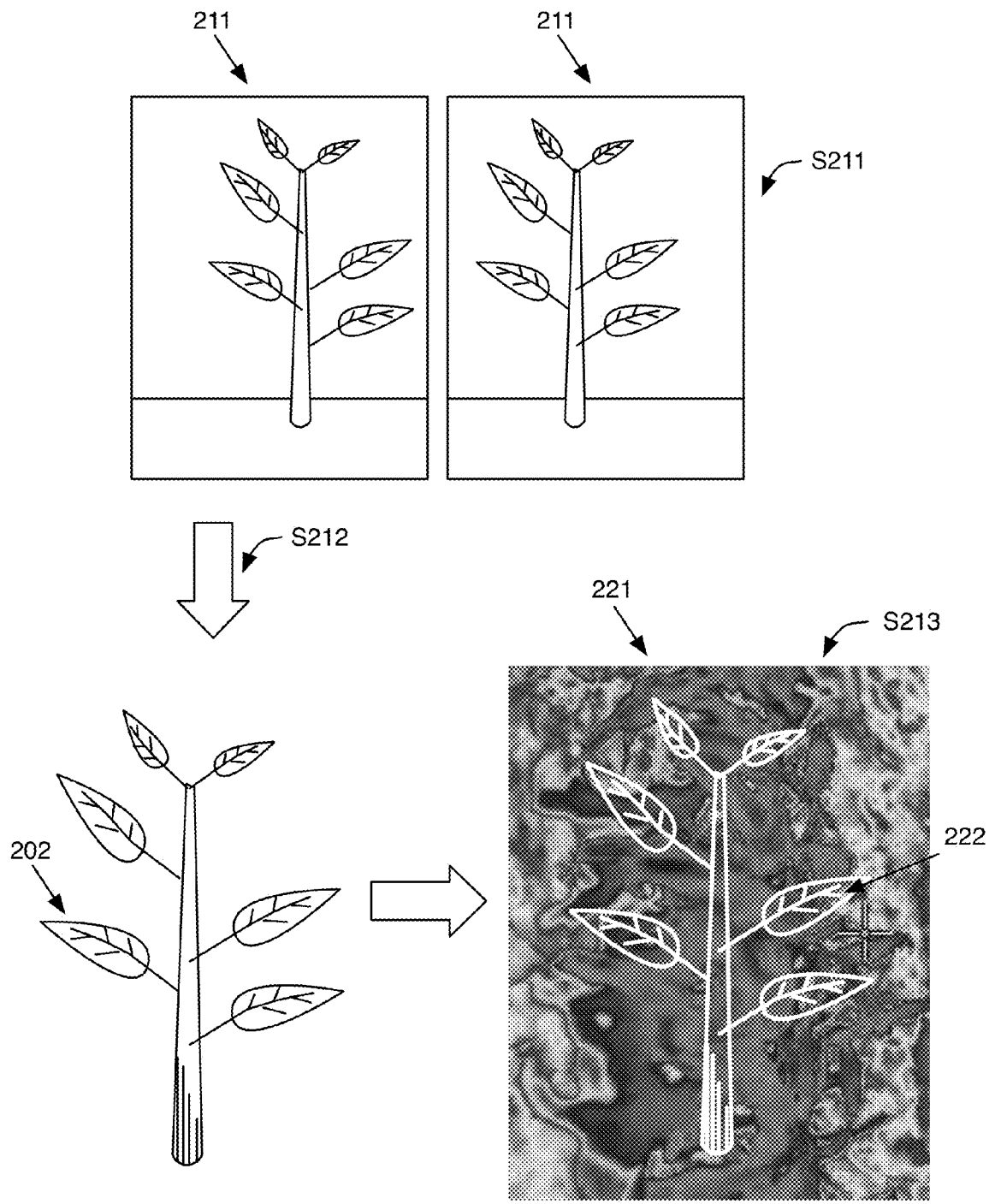
FIG. 17 is a schematic representation of a variation of identifying the plant pixels in the physiological measurement using the 3-D virtual model.

In a fourth variation, the method determines the physiology measurement signals associated with the plant based on the 3-D virtual model. In a first embodiment, as shown in FIG. 17, the physiology measurement is overlaid on the model, based on the relative positions of the physiological sensor and the morphological sensor that took the measurements from which the model was generated. In a second embodiment, a geographic location is used to determine the set of plant pixels. In this embodiment, the method can include determining the geographic locations (e.g., geographic volumetric identifier, including longitude, latitude, and altitude coordinates, relative position relative to a reference point, such as a sensor or marker position, etc.) of a set of points on the plant feature (e.g., based on the geographic location of the recording sensor, the distance of the plant from the sensor, etc.), determining the geographic locations (e.g., geographic volumetric identifier, including longitude, latitude, and altitude coordinates) of a set of pixels within the physiological measurement, and associating (e.g., matching) the set of physiological measurement pixels with the set of plant feature points to identify the plant pixels in the physiological measurement, as shown in FIG. 16. Alternatively, timestamps, odometry, or any other suitable parameter can be used to correlate the virtual model with the physiological measurement. In a third embodiment, the method can include identifying a plant feature in the physiological measurement, identifying the corresponding plant feature within the virtual model, and overlaying the physiological measurement on the virtual model by aligning the identified plant features in the physiological measurement and the virtual model. However, the virtual model can be used to identify the plant pixels in the physiological measurement in any other suitable manner.

The method can additionally include collecting ambient environment parameter values. The ambient environment parameter values are preferably concurrently collected with the physiological measurements and the morphological measurements, but can alternatively be collected at any other suitable time. The ambient environment measurements are preferably recorded by sensors on the system, but can alternatively be recorded by remote sensors, wherein the measurements can be sent to the system or the computing system (on board or remote). However, the ambient environment measurements can be collected in any other suitable manner. In one example, the method includes measuring the sunlight irradiance on the system, wherein the measured sunlight irradiance is preferably used to calibrate the physiology measurement and/or morphology measurement (e.g., intensity of the reflected light).

Processing the measurements to extract a plant parameter S220 functions to extract plant data that characterizes the plant. The plant data can include plant indices (e.g., growth indices, health indices, etc.), plant phenotype, or any other suitable plant parameter.

In a first variation, the method includes calculating the plant parameter value (e.g., plant index value) from the physiological measurement values associated with the plant pixels. The plant index value can be stored in association with a virtual representation of the plant (e.g., a plant identifier, the plant geographic location, the plant virtual model, etc.). In a second variation, the method includes calculating the parameter value for the background pixels (e.g., non-plant pixels) within the physiological measurement, calculating the parameter value for the plant pixels, and correcting or adjusting the plant parameter value with the background parameter value. For example, the NDVI of the plant can be calculated from the plant pixels, the number of leaf layers can be determined (e.g., estimated or determined from the growth history), and the NDVI and leaf layer number can be applied to a calibration curve to correct for soil response. In a third variation, the method includes calculating the plant parameter value (e.g., plant index value) from the physiological measurement values associated with the plant pixels and correcting or adjusting the plant parameter value based on ambient environment parameter values. In a fourth variation, the method includes calculating the plant parameter value and correcting or adjusting the plant parameter value based on a morphological measurement value, such as an estimated or calculated canopy area, leaf area, leaf color, or any other suitable parameter. In a fifth variation, the method includes calculating the plant parameter value based on a rate or magnitude of physiological parameter change. In this variation, the physiological parameter value is determined from each of a series of physiological measurements associated with a plant (e.g., associated with a geographical location or other plant identifier), wherein each physiological measurement is associated with a different timestamp separated by at least a threshold time duration (e.g., at least 1 minute, 1 day, 1 week, 1 month, etc.), and the plant parameter is calculated from the resultant set of physiological parameter values. However, the plant parameter value can be otherwise determined In one example, an image (e.g., video frame or picture) of the plant can be analyzed to determine the size of the plant, the plant color, and the plant shape, while hyperspectral data can be used to determine the NDVI (Normalized Difference Vegetation Index) for the plant or a portion of the plant (or the area of the plant field associated with a plant). Image data is preferably binarized to segment the foreground (indicative of a plant) from the background and to extract characteristics the plant or the area of the plant field associated with the plant. The binarization is preferably used as a mask such that only pixels that correspond to the foreground are analyzed. The foreground can be segmented based on differences in depth (e.g., wherein the foreground is determined to be closer to the viewing plane), colorfulness, chroma, brightness, or any other suitable image parameter or measured parameter. The characteristics can be extracted using a set threshold, a temporal average filter, running a Gaussian average, running a Gaussian mixture model classifier, or through any other suitable detection or segmentation method. In one variation, the plant-pixels are converted to the HSV color-space so that conspicuous saturation in green is indicative of the presence of plant material. In another variation, the image can be filtered for excessive red colorization and excessive green colorization.

Processing the measurements can additionally include identifying shadows, which introduce noise into the plant data measurements. In one variation, identifying shadows includes determining the angle of incident sunlight and estimating where shadows would fall, based on historical location records of plants adjacent the plant currently being measured and the measured or estimated height of the respective plant (e.g., for adjacent plant shadows), the system dimensions (e.g., for system shadows), or any other suitable information. However, the shadows can be otherwise determined and the measurements accordingly corrected.

The method can additionally include identifying a plant within the plant field that expresses a desired phenotype S300, which functions to identify a plant having the desired characteristics. More preferably, identifying the plant functions to identify the one or more plants within the digital plant catalogue that expresses the desired phenotype. However, identifying the plant can include physically identifying the plant within the field or otherwise identifying the plant. The desired phenotype or parameters describing the desired phenotype are preferably received from a user, but can alternatively be automatically determined. The plant of interest can be determined from data collected in a singular session (e.g., the plant is selected after one system pass over the plant field) as shown in FIG. 18, or can be determined from data collected over multiple sessions, wherein each session is associated with a different timestamp (e.g., the plant is selected based on multiple data points, each representing a different time point, for the same plant) as shown in FIG. 19.

Figure 18:
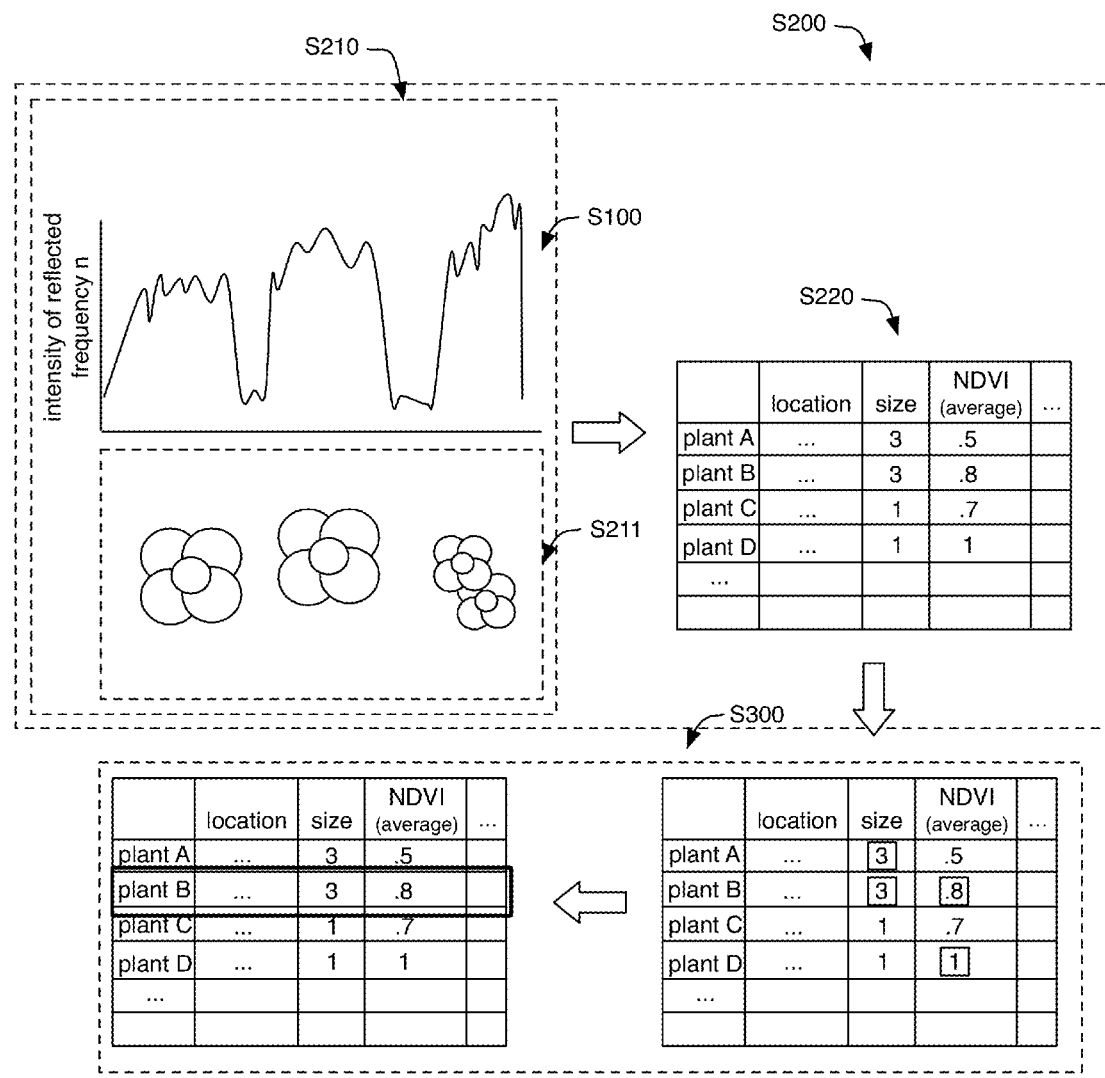
FIG. 18 is a schematic representation of a variation of the method.
Figure 19:
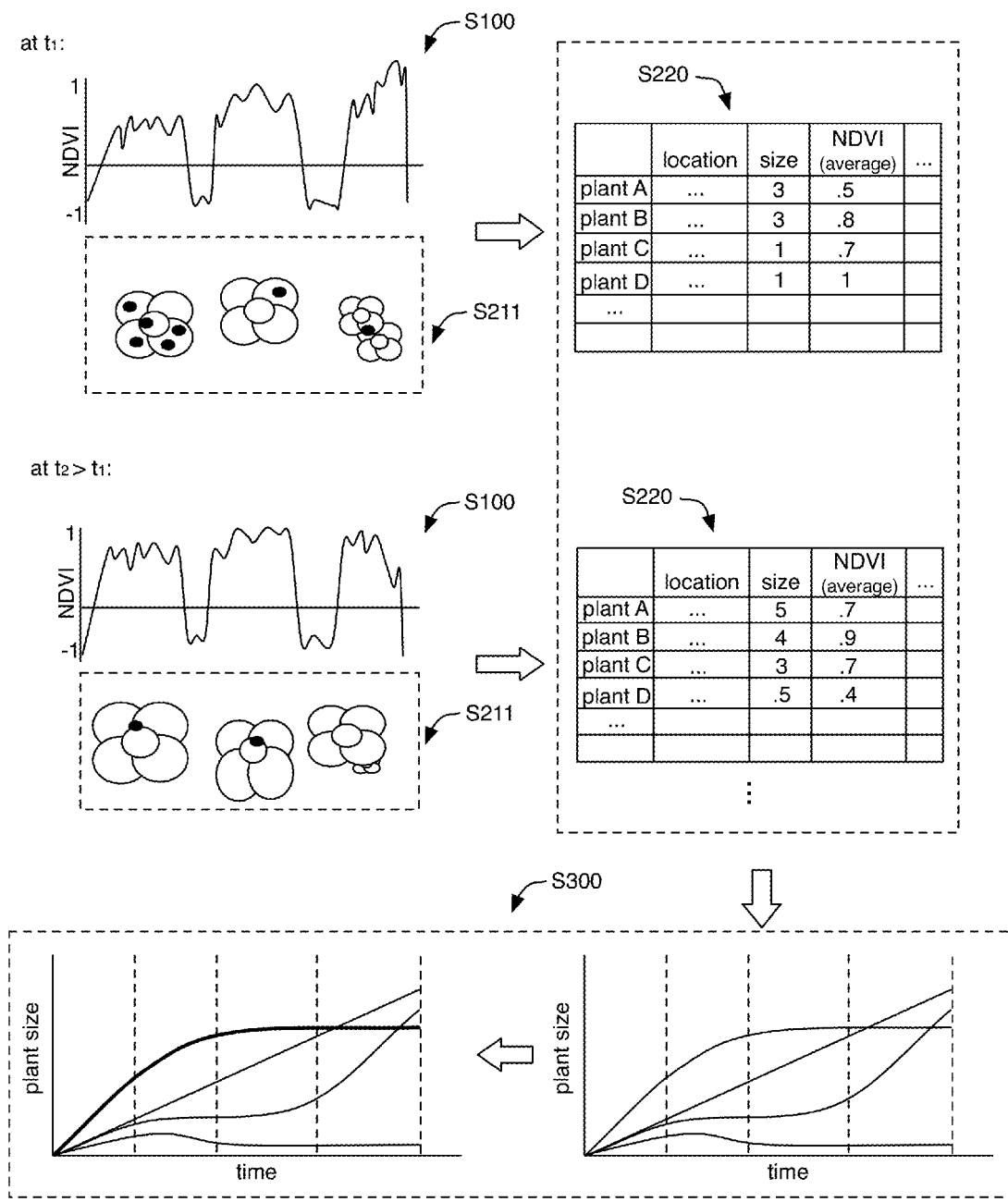
FIG. 19 is a schematic representation of a second variation of the method.

The parameters describing the desired phenotype can include a plant index over or under a predetermined threshold, a plant characteristic value over a characteristic threshold, a desired or threshold combination of plant characteristics (e.g., as shown in FIG. 18), a desired or threshold rate of change in one or more plant characteristics (e.g., as shown in FIG. 19), or any other suitable metric derived from the plant characteristics. For example, plants expressing a desired color (e.g., over a given intensity threshold, within a given hue window, etc.), NDVI, leaf area, cross-sectional plant area, height, individual plant density, germination rate, plant growth density (e.g., number of plants per unit area), root structure, fruit density, fruit color, number of leaves, growth speed, growth stage, internal nutrient level or any other suitable characteristic can be selected for. In another example, plants growing above or below a threshold growth rate, changing color above or below a threshold color change rate, changing cross-sectional shape above or below a threshold shape change rate, developing roots faster or slower than a threshold root growth rate, developing fruit faster or slower than a threshold fruit growth rate, depleting soil water slower than a threshold rate, or having any other suitable characteristic change above or below a threshold change rate or a combination of rates can be selected. However, the plants can be selected based on any other suitable phenotype metric that can be derived from the plant data.

The identified plants can be subsequently harvested, wherein the method can include providing the plant location to the user, or can include harvesting the seeds of the plant, wherein a plant component (e.g, fruits, seeds, leaves, the entire plant, etc.) are harvested (e.g., retrieved) during a subsequent pass over the plant field. Automatically harvesting the seeds can include extracting the seeds while leaving the plant otherwise substantially intact, harvesting the seed by substantially rendering the plant undesirable for harvest, or by harvesting the plant. The method can additionally include determining the development stage of the plant based on the collected data, and determining or estimating the ideal harvesting time. The method can additionally include recording and monitoring the plants that were grown from the extracted seeds, and adjusting the harvesting time and/or harvesting method based on how well the extracted seeds expressed the desired phenotype.

The method can additionally include recording management data, which functions to enable correlation between a treatment received by the plant and the subsequent plant response. Recording management data can additionally or alternatively include detecting a significant difference between different management practices for a given variable. Because this method tracks plant growth on a plant-by-plant basis, the method can enable determination of how different plant phenotypes react to a given treatment.

The method can additionally include treating the plants with the system. The plants are preferably treated before, during, or after plant parameter measurement in the same session, but can alternatively be treated in a separate session. The plants are preferably treated by the same system as the system taking the measurements, but can alternatively be treated by a separate system. In one variation of the method, each plant is treated based on the measurements recorded in the same session, wherein the measurements are processed by the system in real-time to determine the individual plant treatment to obtain a predetermined goal. Predetermined goals can include a target parameter range (e.g., target size range), a target date at which the plant will be in a predetermined growth stage (e.g., a target ripening date), or any other suitable target parameter. In a second variation of the method, each plant is treated based on a predetermined management plan determined for the given plant, for the given plant genotype, or for any other suitable shared plant parameter. In a third variation of the method, each plant is treated based on the historic measurements for the given plant.

However, this method can include any additional method of analyzing and utilizing individual plant data collected in a single session or over time to select a plant based on the characteristics of the expressed plant phenotype.

As a person skilled in the art will recognize from the previous detailed description and from the figures and claims, modifications and changes can be made to the preferred embodiments of the invention without departing from the scope of this invention defined in the following claims.

We claim:

1. A system for plant parameter detection, comprising:
    a plant morphology sensor directed in a first direction toward a volume and configured to record a morphology measurement of a plant, the plant including a plant portion, the volume including an ambient environment adjacent the plant, the morphology measurement including data describing a structure or geometry of the plant;
    a plant physiology sensor directed in a second direction toward the volume and configured to record a plant physiology measurement of the plant portion and an ambient environment adjacent the plant, the plant physiology measurement including data describing a functionality of a plant and comprising a set of physiology pixels;
    a computing system configured to:
        identify a subset of the set of physiology pixels based on the structure or geometry described by the morphology measurement, the subset of physiology pixels being associated with the plant portion within the physiology measurement;
        determine physiology values for each pixel of the subset of physiology pixels; and
        extract a plant index based on the physiology values of the subset.

2. The system of claim 1, further comprising an ambient environment sensor, the ambient environment sensor comprising a photosensor configured to measure incident sunlight parameters, wherein the computing system is further configured to adjust the physiology values based on the incident sunlight parameters measured by the ambient environment sensor.

3. The system of claim 2, wherein the photosensor comprises a pyranometer.

4. The system of claim 2, wherein the system further comprises a light source arranged proximal to the physiology sensor and configured to emit light along a vector along the second direction, wherein the morphology measurement and the physiology measurement are based on reflected emitted light.

5. The system of claim 2, wherein the ambient environment sensor further comprises a plant thermal sensor and an ambient temperature sensor.

6. The system of claim 1, wherein the plant morphology sensor comprises an RGB camera and the physiology sensor comprises a narrow band multispectral camera.

7. The system of claim 6, wherein the physiology sensor comprises:
    a first narrow band multispectral camera configured to capture image data at a 550 nm band;
    a second narrow band multispectral camera configured to capture image data at a 650 nm band; and
    a third narrow band multispectral camera configured to capture image data at a 800 nm band.

8. The system of claim 1, further comprising a second plant morphology sensor configured to record a second morphology measurement, wherein the computing system is further configured to:
    identify a plant feature within the second morphology measurement;
    determine a set of geographic locations associated with the plant feature; and
    determine the subset of pixels based on pixels in the set of physiology pixels associated with the set of geographic locations.

9. The system of claim 8, wherein the second plant morphology sensor is arranged in a position within a field of view of the first plant morphology sensor.

10. The system of claim 1, wherein the computing system is further configured to:
    generate a three-dimensional model of a plant portion based on the morphology measurement; and
    identify the subset of physiology pixels by comparing the set of physiology pixels with the three-dimensional model generated based on the morphology measurement.

11. The system of claim 10, wherein the computing system identifies the subset of physiology pixels by:
    determining a geographic volumetric identifier for each of a set of points within the three-dimensional model; and
    identifying a set of pixels within the physiology measurement sharing the determined geographic volumetric identifiers.

12. The system of claim 10, wherein the computing system is further configured to:
    determine ambient environment pixels within the set of physiology pixels corresponding to an ambient environment of the plant, based on the three-dimensional model of the plant portion;
    determine ambient environment index values for the ambient environment pixels based on the physiology measurement; and
    correct the physiology value for the set of physiology pixels based on the ambient environment index values.

13. The system of claim 10, wherein the computing system is further configured to:
    calculating the plant index at first and second timepoints for the plant;
    determining a growth parameter value for the plant based on changes in the plant index between the first and second timepoints.

14. The system of claim 13, wherein the growth parameter value for the plant is determined based on changes in the three-dimensional model of the plant portion between the first and second timepoints, determined from respective morphology measurements.

15. The system of claim 1, wherein the morphology measurement comprises a color image, and the physiology measurement comprises a set of narrow-band spectral images.

16. The system of claim 1, wherein the morphology measurement and the physiology measurement are recorded concurrently.

17. A method for plant parameter determination, comprising:
receiving a morphology measurement of a first geographic area from a morphology sensor, the morphology measurement indicative of plant structure or geometry;
generating a three-dimensional model of a plant portion based on the morphology measurement;
receiving a physiology measurement of the first geographic area from a physiology sensor, the physiology measurement indicative of a plant functionality and comprising a set of physiology pixels;
identifying a subset of the set of physiology pixels from the physiology measurement by comparing the set of physiology pixels with the three-dimensional model generated based on the morphology measurement, the subset of physiology pixels corresponding to the plant portion;
determining physiology values for each pixel of the subset of physiology pixels; and
calculating a plant index value for the plant portion based on the physiology values for each pixel of the subset of physiology pixels.

18. The method of claim 17, wherein, wherein identifying the subset of physiology pixels corresponding to the plant portion comprises:
determining a geographic volumetric identifier for each of a set of points within the model; and
identifying a set of pixels within the physiology measurement sharing the determined geographic volumetric identifiers.

19. The method of claim 17, further comprising:
determining ambient environment pixels within the set of physiology pixels corresponding to an ambient environment of the plant, based on the three-dimensional model of the plant portion;
determining ambient environment index values for the ambient environment pixels based on the physiology measurement; and
correcting the physiology value for the set of physiology pixels based on the ambient environment index values.

20. The method of claim 17, further comprising:
repeating the method at first and second timepoints for the plant;
determining a growth parameter value for the plant based on changes in the plant index value between the first and second timepoints.

21. The method of claim 20, further comprising determining the growth parameter value for the plant based on changes in the three-dimensional model of the plant portion between the first and second timepoints, determined from the respective morphology measurements.

22. The method of claim 17, wherein the morphology measurement comprises a color image, and the physiology measurement comprises a set of narrow-band spectral images.

23. The method of claim 17, wherein the morphology measurement and the physiology measurement are recorded concurrently.

24. The method of claim 17, wherein the morphology measurement and physiology measurement have different fields of view.

25. The method of claim 17, further comprising adjusting the physiology values for each of the subset of physiology pixels based on incident sunlight parameters measured by a photosensor.

26. The method of claim 17, further comprising emitting light, from a light source, along a vector along a direction of the physiology sensor, and wherein the morphology measurement and the physiology measurement are based on reflected emitted light.

27. The method of claim 17, wherein the morphology measurement comprises a measurement from an RGB camera and physiology measurement comprises a measurement from a narrow band multispectral camera.

28. The method of claim 27, wherein the physiology measurement comprises image data at a 550 nm band, image data at a 650 nm band, and image data at a 800 nm band.

29. The method of claim 17, further comprising:
receiving a second morphology measurement from a second morphology sensor;
identifying a plant feature within the second morphology measurement;
determining a set of geographic locations associated with the plant feature; and
determining the subset of pixels based on pixels in the set of physiology pixels associated with the set of geographic locations.

30. The method of claim 29, wherein the second morphology measurement measures a second geographic area that overlaps with the first geographic area.

* * * * *

UNITED STATES PATENT AND TRADEMARK OFFICE
CERTIFICATE OF CORRECTION

PATENT NO. : 9,658,201 B2
APPLICATION NO. : 14/329161
DATED : May 23, 2017
INVENTOR(S) : Lee Kamp Redden and Matthew Colgan Page 1 of 1

It is certified that error appears in the above-identified patent and that said Letters Patent is hereby corrected as shown below:

In the Claims

Column no: 33, Line(s): 42-43, Claim 1: "pixels; a computing system," to read as --pixels; and a computing system--

Column no: 34, Line(s): 58, Claim 13: "configured to: calculating" to read as --configured to: calculate--

Column no: 34, Line(s): 59-60, Claim 13: "plant; determining" to read as --plant; and determining--

Column no: 34, Line(s): 60, Claim 13: "determining a growth parameter" to read as --determine a growth parameter--

Column no: 36, Line(s): 3-4, Claim 20: "plant; determining" to read as --plant; and determining--

Signed and Sealed this
Thirty-first Day of July, 2018

Andrei Iancu
*Director of the United States Patent and Trademark Office*